(12) United States Patent
Thompson et al.

(10) Patent No.: US 7,457,708 B2
(45) Date of Patent: *Nov. 25, 2008

(54) METHODS AND DEVICES FOR IDENTIFYING RELATED IONS FROM CHROMATOGRAPHIC MASS SPECTRAL DATASETS CONTAINING OVERLAPPING COMPONENTS

(75) Inventors: Dean R. Thompson, Fort Collins, CO (US); William M. Old, Boulder, CO (US); David Lee Gines, Fort Collins, CO (US)

(73) Assignee: Agilent Technologies Inc, Santa Clara, CA (US)

( * ) Notice: Subject to any disclaimer, the term of this patent is extended or adjusted under 35 U.S.C. 154(b) by 772 days.

This patent is subject to a terminal disclaimer.

(21) Appl. No.: 10/603,053

(22) Filed: Jun. 24, 2003

(65) Prior Publication Data
US 2004/0181351 A1  Sep. 16, 2004

Related U.S. Application Data

(63) Continuation-in-part of application No. 10/388,088, filed on Mar. 13, 2003.

(51) Int. Cl.
*G06F 19/00* (2006.01)
*G01N 24/00* (2006.01)
(52) U.S. Cl. .................................... 702/19; 436/173
(58) Field of Classification Search ................. None
See application file for complete search history.

(56) References Cited
U.S. PATENT DOCUMENTS

| 4,353,242 A | 10/1982 | Harris et al. |
| 5,175,430 A | 12/1992 | Enke et al. |
| 5,247,175 A | 9/1993 | Schoen et al. |
| 5,453,613 A | 9/1995 | Gray et al. |
| 5,672,869 A | 9/1997 | Windig et al. |
| 6,524,803 B2 | 2/2003 | Overney et al. |
| 2002/0053545 A1 | 5/2002 | van der Greef |
| 2002/0063208 A1 | 5/2002 | Hastings |
| 2003/0078739 A1 | 4/2003 | Norton et al. |
| 2003/0109990 A1 | 6/2003 | Axelsson |
| 2004/0096982 A1 | 5/2004 | Barnea et al. |

OTHER PUBLICATIONS

Lingjun Li, et al., High-Throughput Peptide Identification from Protein Digests Using Data-Dependent Multiplexed Tandem FTICR Mass Spectrometry Couple with Capillary Liquid Chromatography, Analytical Chemistry, Jul. 15, 2001, pp. 3312-3322, vol. 73, No. 14, American Chemical Society, Published on Web Jun. 14, 2001.

Cliona M. Fleming, et al., Windowed mass selection method: a new data processing algorithm for liquid chromatography—mass spectrometry data, Journal of Chromatography, 1999, pp. 71-85, Elsevier Science B.V.

Christophe Masselon, et al., Accurate Mass Multiplexed Tandem Mass Spectrometry for High-Throughput Polypeptide Identification from Mixtures, Analytical Chemistry, Apr. 15, 2000, pp. 1918-1924, vol. 72, No. 8, American Chemical Society, Published on Web Mar. 17, 2000.

*Primary Examiner*—Lori A Clow

(57) ABSTRACT

Described are techniques for processing data sets produced by analyzing a sample. The input data set is represented as rows of intensities over time for a particular mass to charge (m/z) range. A correlation matrix is produced in which each row of the input data set is correlated with every other row in the input data set. The correlation matrix is clustered or grouped such that those highly correlated m/z ranges are included in the same group. A set of one or more scans is selected for each group representing periods of interest within each group. Using the m/z values included in each cluster, a resultant sample spectra is created for each of the selected scans. The processing techniques may be used to identify parent and related fragment ions in the input data set and as a preprocessor producing resultant sampled spectra used as input to subsequent processing.

40 Claims, 17 Drawing Sheets

US 7,457,708 B2

METHODS AND DEVICES FOR IDENTIFYING RELATED IONS FROM CHROMATOGRAPHIC MASS SPECTRAL DATASETS CONTAINING OVERLAPPING COMPONENTS

RELATED APPLICATIONS

This application is a continuation-in-part of, U.S. patent application Ser. No. 10/388,088, filed Mar. 13, 2003, entitled "Methods and Devices for Identifying Biopolymers Using Mass Spectroscopy", Dean R. Thompson and Steven M. Fischer, which is incorporated herein by reference in its entirety.

BACKGROUND

1. Technical Field

This application is related to mass spectral analysis, and more particularly to processing mass spectra generated by mass spectral analysis.

2. Description of Related Art

Mass spectroscopy is a powerful analytical tool that may be used in identifying unknown compounds as well as their quantities. Mass spectroscopy may also be useful, for example, in elucidating the structure and chemical properties of molecules, and may be used in connection with organic as well as inorganic substances. The identification of proteins and other molecules in a complex mixture derived from biological sources may be performed using mass spectroscopy. A variety of different techniques have been developed for use with the identification of molecules, such as proteins.

Prior to performing mass spectroscopy, one technique separates various proteins in the mixture using two-dimensional gel electrophoresis (2DE). The resulting spots may be excised and digested to break the proteins into shorter polypeptide chains. These digests may be analyzed via mass spectroscopy and the resulting spectrum compared to spectra predicted from amino acid sequences and information included in databases. The foregoing technique has difficulty, for example, in resolving highly acidic and hydrophobic proteins.

In order to overcome the foregoing difficulties in the first technique, efforts have been made to perform the separation of such mixtures via high performance liquid chromatography (HPLC). These efforts include digesting all of the proteins in the mixture prior to attempting separation techniques resulting in a hyper-complex mixture. Using such a hyper-complex mixture, it may be neither practical nor possible to provide a complete and perfect separation. Rather, the eluate entering the mass spectrometer may have multiple peptides present at any point in time such that multiple peptides co-elute resulting in mass spectra that may contain a mixture of ions from the various peptides present.

The foregoing may be further complicated by two additional factors. First, large molecules such as peptides may tend to collect a lot of charge during electro-spray ionization. As a result of the electro-spray ionization and the collection of a large charge, the spectrum of each peptide may have multiple peaks corresponding to the multiple charge states. Additionally, high-resolution mass spectrometers, such as the time of flight devices, may resolve multiple isotope peaks for each charge state. As a result of the above factors, a very complex spectrum may result.

In order to reduce the complexity of the resulting spectra, techniques, such as charge assignment and de-isotoping, may be performed. However, these techniques may be sensitive to various types of interference and noise, chemical as well as electrical.

Additionally, a complete data set of spectra produced by, for example, liquid chromatography/mass spectrometry processing (LC/MS) may be quite large. A spectrum may be taken at various frequencies, such as several times a second or every few seconds, over a period of several hours. The size of such a data set presents a number of challenges in accordance with analyzing such a large amount of data.

One technique to reduce the computational burden in connection with such large amounts of data is to only select particular spectra to be analyzed in detail in accordance with particular criteria. However, these spectra are typically selected manually by visual inspection of the chromatographic data, which may be time consuming, clumsy, and error prone.

Accordingly, it may be desirable to provide a technique for analyzing chromatographic information, such as may be included in an LC/MS dataset, and using the resulting analysis information to separate related ions into spectra representing individual compounds. It may also be desirable to use the resulting analysis information to identify the particular spectra that provide maximum signal levels for subsequent analysis. It may also be desirable to remove and filter noise from the data and significantly reduce the size and complexity of the dataset to be analyzed. It may also be desirable to use such a technique in connection with protein identification as well as be generally applicable for the analysis of other classes of molecules sharing similar characteristics.

SUMMARY OF THE INVENTION

In accordance with one aspect of the invention is a method for identifying related ions in an input data set produced by analyzing a sample comprising: correlating each row of data in an input data set with every other row of data in said input data set producing a correlation matrix, each row representing intensities over time for a particular mass to charge (m/z) range, each element of said correlation matrix including a correlation value and having associated row and column identifiers identifying which rows in said input data set are associated with said correlation value; clustering said correlation matrix identifying at least one group and at least one row of said correlation matrix as being in said at least one group, each group representing covarying chromatograms; selecting at least one time period of interest for each group; and producing a resultant spectrum for each group by sampling chromatograms included in each of said groups at each of said at least one time period of interest of using a form of said input data set.

In accordance with another aspect of the invention is a method for quantifying at least one ion in an input data set produced by analyzing a sample comprising: correlating each row of data in an input data set with every other row of data in said input data set producing a correlation matrix, each row representing intensities over time for a particular mass to charge (m/z) range, each element of said correlation matrix including a correlation value and having associated row and column identifiers identifying which rows in said input data set are associated with said correlation value; clustering said correlation matrix identifying at least one group and at least one row of said correlation matrix as being in said at least one group, each group representing chemically related components exhibiting correlated chromatographic behavior; selecting at least one time period of interest for each group; and producing a resultant spectrum for each group by sampling chromatograms included in each of said groups at each of said at least one time period of interest of using a form of said input data set.

In accordance with another aspect of the invention is a computer program product for identifying related ions in an input data set produced by analyzing a sample comprising: machine executable code that correlates each row of data in an input data set with every other row of data in said input data set producing a correlation matrix, each row representing intensities over time for a particular mass to charge (m/z) range, each element of said correlation matrix including a correlation value and having associated row and column identifiers identifying which rows in said input data set are associated with said correlation value; machine executable code that clusters said correlation matrix identifying at least one group and at least one row of said correlation matrix as being in said at least one group, each group representing covarying chromatograms; machine executable code that selects at least one time period of interest for each group; and machine executable code that produces a resultant spectrum for each group by sampling chromatograms included in each of said groups at each of said at least one time period of interest of using a form of said input data set.

In accordance with yet another aspect of the invention is a computer program product for quantifying at least one ion in an input data set produced by analyzing a sample comprising: machine executable code that correlates each row of data in an input data set with every other row of data in said input data set producing a correlation matrix, each row representing intensities over time for a particular mass to charge (m/z) range, each element of said correlation matrix including a correlation value and having associated row and column identifiers identifying which rows in said input data set are associated with said correlation value; machine executable code that clusters said correlation matrix identifying at least one group and at least one row of said correlation matrix as being in said at least one group, each group representing chemically related components exhibiting correlated chromatographic behavior; machine executable code that selects at least one time period of interest for each group; and machine executable code that produces a resultant spectrum for each group by sampling chromatograms included in each of said groups at each of said at least one time period of interest of using a form of said input data set.

BRIEF DESCRIPTION OF THE DRAWINGS

Features and advantages of the present invention will become more apparent from the following detailed description of exemplary embodiments thereof taken in conjunction with the accompanying drawings in which.

DETAILED DESCRIPTION OF EMBODIMENT(S)

Figure 1:
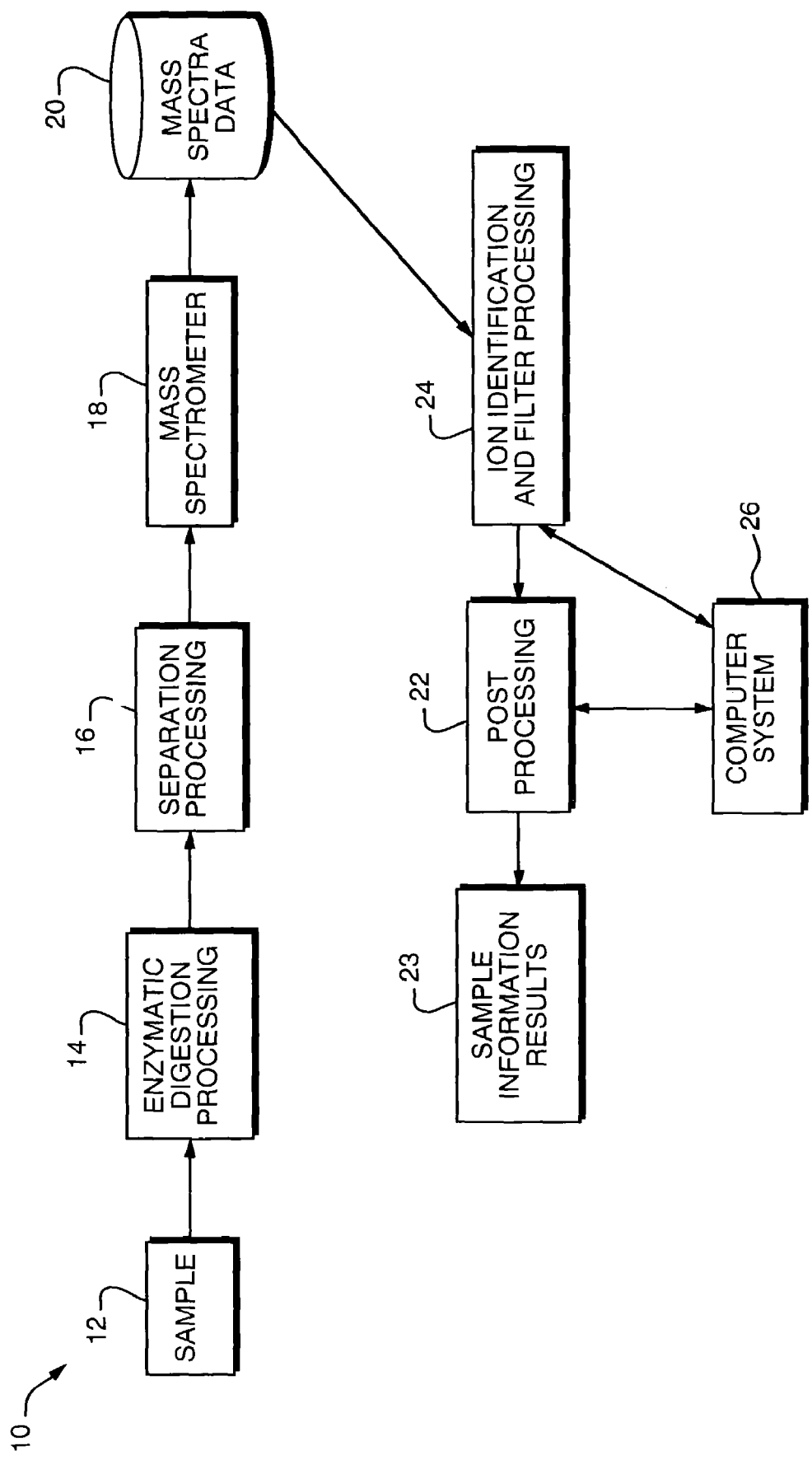
FIG. 1 is an example of a block diagram illustrating processing steps of a substance input to a mass spectrometer.

Referring now to FIG. 1, shown is an example of a block diagram of processing steps that may be performed in connection with identification of a molecule within a mixture in an embodiment. In this particular example, the substance may be a mixture of one or more molecules, for example, such as peptides or proteins, being processed for identification. It should be noted that the techniques described herein may also be used in performing a quantitative analysis of molecules in a sample. An input sample or substance 12 is digested in the enzymatic digestion processing 14. This enzymatic digestion processing 14 breaks the proteins in the sample 12 into shorter polypeptide chains. Subsequently, the digests may then be separated via a separation processing technique 16. Any one of a variety of different separation processing techniques may be used such as liquid chromatography, 2D Gel separation, and the like. It should be noted that generally any separation technique and/or digestion technique may be used to separate the various polypeptides in accordance with, for example, molecular weight, electrical fields and the like.

After separation processing 16, the resulting separations may be input to a mass spectrometer 18 producing mass spectra data 20 as an output. The mass spectra data may be input to ion identification and filter processing 24. The ion identification and filter processing 24 may use a computer system 26 in connection with performing processing steps therein. Details about the specific processing steps performed in connection with the ion identification and filter processing 24 are described elsewhere herein in more detail. Subsequently, output of the ion identification and filtering processing 24 may serve as an input to post-processing 22.

Post-processing 22 may include, for example, performing de-isotoping or charge assignment. Post-processing 22 may also include for example, comparison of monitored output data to known spectral data, for example, in order to identify a particular known type and quantity associated with proteins and the like that may be included in the sample 12. The post-processing 22 may also use the computer system 26. It should be noted that post-processing 22 may use the same or different computer system used in connection with the processing steps of the ion identification and filter processing 24. As an output of post processing, sample information results 23 may be produced. The results 23 may include, for example, types of known proteins and quantities identified in the sample 12.

It should be noted that, although the particular sample or substance 12 described in the foregoing and throughout this example may be a protein, the techniques described herein may be used in connection with other types of substances or samples 12 to identify other molecules and/or associated quantities. An embodiment may include additional and different processing steps than those described herein in accordance with the type of sample or substance 12 being analyzed as well as the particular components being identified within the sample or substance. This may affect the processing steps performed both before and after processing by the mass spectrometer. For example, the enzymatic digestion processing may not be used in connection with performing an analysis of a sample or substance that does not include proteins.

Figure 2:
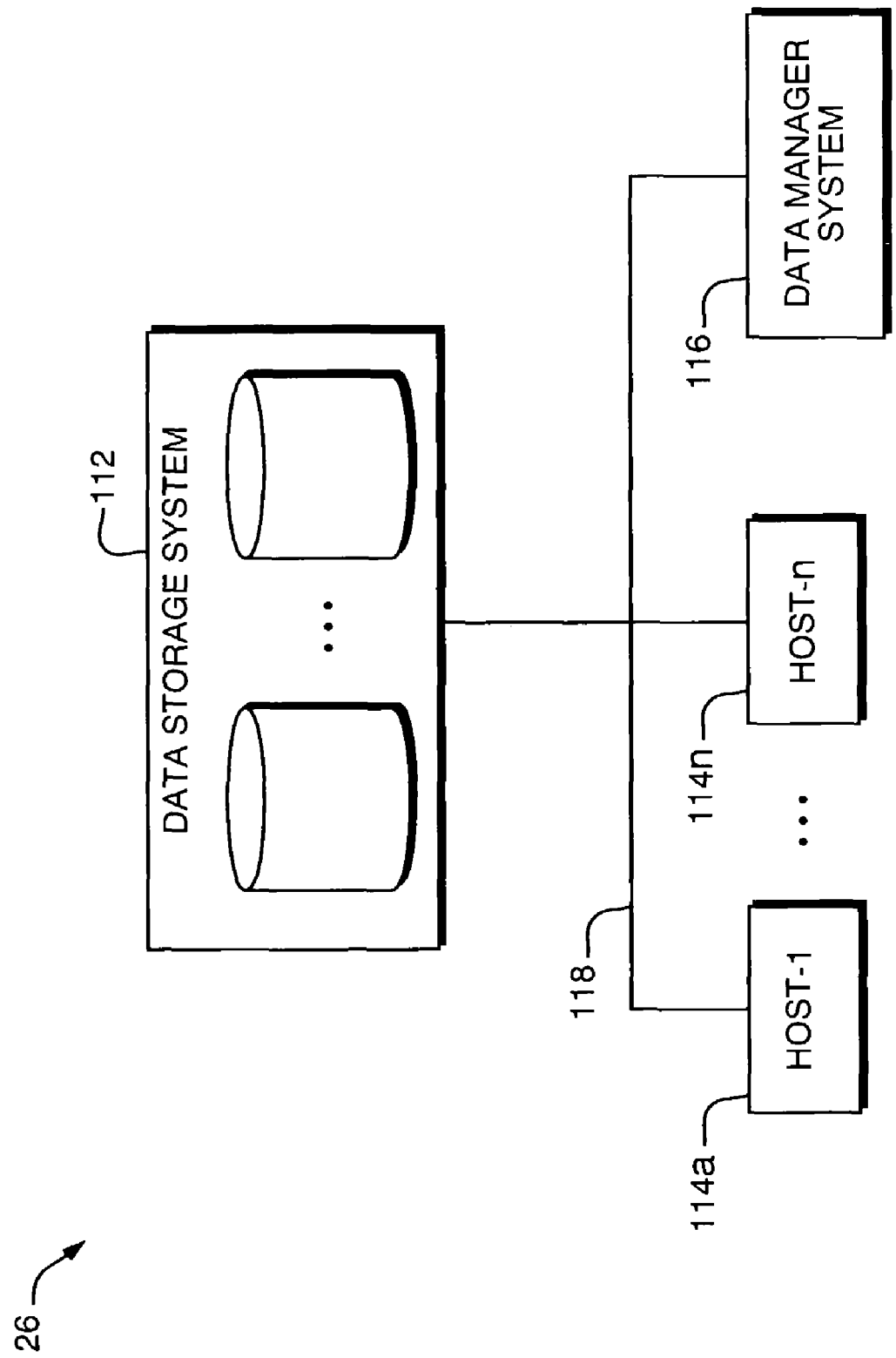
FIG. 2 is an example of an embodiment of a computer system included in FIG. 1.

Referring now to FIG. 2, shown is a more detailed example of an embodiment of the computer system 26. It should be noted that FIG. 2 illustrates only one particular arrangement of a computer system that may be included in the embodiment 10 of FIG. 1.

The computer system 26 includes a data storage system 112 connected to host systems 114a-114n, and a data manager system 116 through communication medium 118. In this embodiment of the computer system 26, the N hosts 114a-114n and the data manager system 116 may access the data storage system 112, for example, in performing input/output (I/O) operations or data requests. The communication medium 118 may be any one of a variety of networks or other type of communication connections as known to those skilled in the art. The communication medium 118 may be a network connection, bus, and/or other type of data link, such as a hardwire or other connections known in the art. For example, the communication medium 118 may be the Internet, an intranet, network or other connection(s) by which the host systems 114a-114n, and the data manager system may access and communicate with the data storage system 112, and may also communicate with others included in the computer system 26.

Each of the host systems 114a-114n, the data manager system 116, and the data storage system 112 included in the computer system 26 may be connected to the communication medium 118 by any one of a variety of connections as may be provided and supported in accordance with the type of communication medium 118. The processors included in the host computer systems 114a-114n and the data manager system 116 may be any one of a variety of commercially available single or multi-processor system, such as an Intel-based processor, IBM mainframe or other type of commercially available processor able to support incoming traffic in accordance with each particular embodiment and application.

It should be noted that the particulars of the hardware and software included in each of the host systems 114a-114n and the data manager system 116, as well as those components that may be included in the data storage system 112 may vary with each particular embodiment. Each of the host computers 114a-114n, as well as the data manager system 116, may all be located at the same physical site, or, alternatively, may also be located in different physical locations. Examples of the communication medium that may be used to provide the different types of connections between the host computer systems, the data manager system, and the data storage system of the computer system 26 may use a variety of different communication protocols such as SCSI, ESCON, Fibre Channel, or GIGE (Qigabit Ethernet), and the like. Some or all of the connections by which the hosts, data manager system 116 and data storage system 112 may be connected to the communication medium 118 may pass through other communication devices, such as a Connectrix or other switching equipment that may exist such as a phone line, a repeater, a multiplexer or even a satellite.

Each of the host computer systems as well as the data manager system may perform different types of data operations in accordance with different types of administrative tasks. In the embodiment of FIG. 2, any one of the host computers 114a-114n may issue a data request to the data storage system 112 to perform a data operation. For example, an application may be invoked in connection with ion identification and filter processing 24 and may execute on one of the host computers 114a-114n.

It should be noted that the computer system 26 included in the system 10 of FIG. 1 may also be a single computer, such as a personal computer, as well as another arrangement of a plurality of computer systems as described above.

Figure 3:
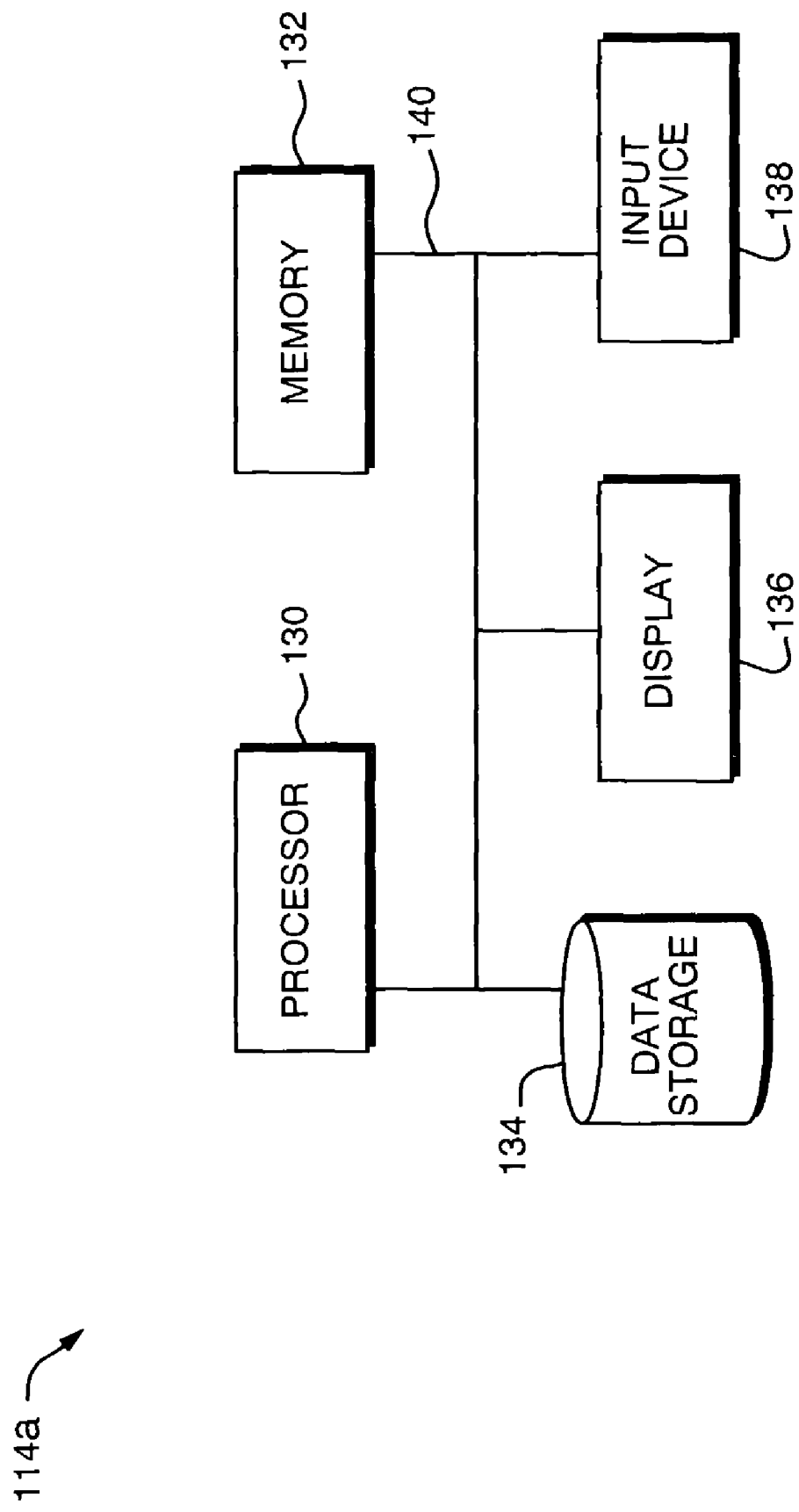
FIG. 3 is an example of an embodiment of a host included in the computer system of FIG. 2.

Referring now to FIG. 3, shown is a more detailed example of an embodiment of a host computer system 114a-114n that may included in the computer system 26. The host computer system 114a may include components such as one or more processors 130, a memory 132, one or more data storage units 134, as well as a display 136, and one or more input devices 138. All of these components within a computer system 114a may communicate and transfer user data and command information using a local bus 140.

It should be noted that the components included for the host computer system 114a may also be those components included in an embodiment in which the computer system 26 is a single computer, for example, such as a single personal computer that may be used in connection with post-processing and ion identification and filter processing 24.

Figure 4:
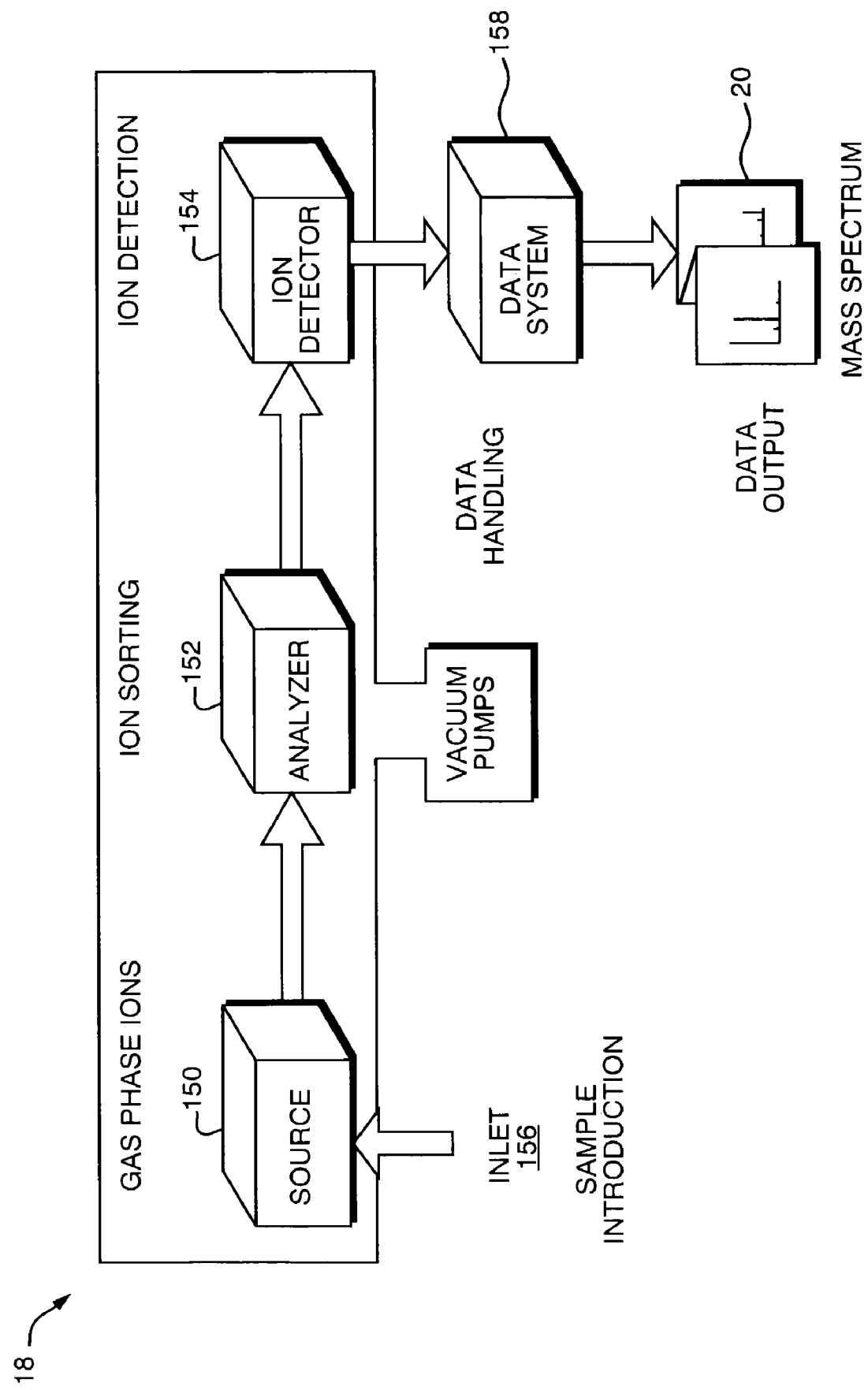
FIG. 4 is an example of a functional block diagram of components included in a mass spectrometer of FIG. 1.

Referring now to FIG. 4, shown is an example of an embodiment of a mass spectrometer 18. A mass spectrometer may be characterized as an instrument that measures the mass to charge ratios of individual molecules that have been converted into ions. As described in the following paragraphs, a mass spectrometer does not actually measure the molecular mass directly, but rather determines the mass-to-charge ratio of the ions formed from a particular molecule or molecules. A useful unit for purposes described herein is a unit referring to a fundamental unit of charge, the magnitude of the charge on an electron. The charge of an ion may be denoted by the integer number z of the fundamental unit of charge and the mass-to-charge ratio may be referred to as m/z.

FIG. 4 includes the different functional units of a mass spectrometer that may be represented conceptually in the block diagram 18 of FIG. 4. A sample may be introduced via an inlet 156 into a vacuum chamber. It should be noted that a sample may be in any one of a variety of different forms including, for example, a liquid solution, embedded in a solid matrix, or a vapor. Depending on the type of inlet and ionization techniques used, the sample may already exist as ions in solution, or it may be ionized in conjunction with its volatilization or by other methods in the ion source 150. In this embodiment, as the sample is introduced into the inlet 156, the sample is placed in a gas phase and then charged to produce ions. The ions are sorted by an analyzer 152 according to their mass-to-charge or m/z ratios and then collected by an ion detector 154. In the ion detector 154, the ion flux may be converted to a proportionate electrical current. Output of the ion detector 154 serves as an input to the data system 158 recording the magnitude of the various electrical signals as a function of the m/z ratios and converting the information into mass spectrometer data 20.

It should be noted that in the foregoing general description regarding a mass spectrometer, different types of mass spectrometers may vary from the components included in FIG. 4. For example, the ion sorting described above may be included in a quadrupole instrument but not in a TOF mass spectrometer since the TOF mass spectrometer measures the flight time of the ions in a fixed length tube. The techniques described herein may be used with any type of mass spectrometer and any description to a particular type of mass spectrometer should not be construed so as to limit the application of the techniques described herein.

It should be noted that an embodiment may include ion selection processing as part of ion sorting 152 in which only a portion of the particular ions are selected for further processing and analysis. As will be shown and described elsewhere herein, the mass spectrum data output from the mass spectrometer 18 is generally a graph of ion intensity on the y axis as a function of the mass-to-charge ratio (m/z) be displayed on the x axis of the spectrum. It should be noted that the ions coming from the mass spectrometer 18 may be positively as well as negatively charged.

As described herein, the sample may be in any one of a variety of forms when introduced into the inlet 156. For example, if the sample is a solid, the sample may be evaporated or sublimed into a gas phase such as, for example, by heating. Gases and liquids may be introduced through inlet designs which control the flow. Some embodiments may combine various techniques in processing, for example, such as volitization and ionization occurring at the same time. The sample may also be a mixture in which the individual components may be separated prior to input and analysis by the mass spectrometer. Separation is described in connection with processing step 16 of FIG. 1. Separation may be used to simplify mass spectra for a sample with multiple components by reducing the number of co-eluting compounds. Gas chromatography may be coupled with mass spectrometry as a means for separation as also described herein. Gas chromatography for example may allow compounds already in a vapor phase to enter the mass spectrometer separated in time so that components of mixtures may be detected and analyzed. Liquid chromatographs may also be used as well as capillary electrophoresis devices and other types of hardware and/or software used in connection with performing the separation processing prior to introduction of a sample into a mass spectrometer 18.

Molecular and fragment ions may be produced in the ion source 150 as shown in FIG. 4. If the input is not already ionized, any one of a variety of different ionization techniques may be used, for example, including electro-spray ionization (ESI). It should be noted that although both positive and negative ions may be generated in the ion source at the same time, a single polarity may be recorded at any particular time. A given mass spectrum may include positive or negative ions. The ions are then input to the ion sorting or analyzer 152. The analyzer may use dispersion or filtering to sort ions according the mass-to-charge ratios or other relative properties. Analyzers may include for example magnetic sectors, quadrupole mass filters, Fourier transform ion cyclotron resonance spectrometers, time of flight mass analyzers and the like. Subsequently, the sorted ions produced by the ion sorter or analyzer 152 are input into the ion detection processing 154 where the particular charge of the ions are determined.

It should be noted that a computer may be used in connection with controlling the mass spectrometer as well as in spectrum acquisition, storage and presentation. As described herein for example in connection with the processing of the block diagram 10 of FIG. 1, software and/or hardware may be used in a computer system in connection with performing quantization, spectral interpretation, and compound identification.

It should be noted that in addition to the ESI technique to generate ions as a result of the source processing 150 within the mass spectrometer, chemical ionization, desorption ionization, electro spray ionization, and the like may be used in connection with performing ionization. It should be noted that for polypeptides, and the like (biomolecules), techniques such as ESI, Matrix Assisted Laser Desorption Ionization (MALDI), Atmospheric-Pressure MALDI (AP-MALDI), and other "soft" ionization techniques are preferred over "hard" ionization techniques. Soft and hard with respect to ionization techniques refer to the energy levels used to ionize the molecules of interest. Hard ionization techniques are not compatible with biomolecules because they result in extensive fragmentation.

Separation techniques, such as gas chromatography (GC), liquid chromatography(LC), and the like as described herein may be used in connection with mass spectrometry in order to identify chemical compounds. In connection with using a mass spectrometer (MS) with a gas or liquid chromatograph, an interface may be used to restrict or reduce the gas flow into the mass spectrometer. For example, this may result in an interface being introduced in between separation processing 16 and mass spectrometer 18 as shown in connection with FIG. 1. Any chromatographic technique, such as, for example, LC, C, FFElectrophoresis, and the like may be used in connection with biomolecules. The use of liquid phase techniques may be preferred due to the ease with which they may be interfaced with a mass spectrometer in addition to the ability to monitor the chromatographic behavior of eluting components.

In connection with GC/MS, LC/MS or other combinations, the output data of the mass spectra 20 consists of a series of mass spectra acquired over time. To generate this information, the mass spectrometer may scan the mass range, for example, for a particular m/z range repeatedly for a particular chromatographic run. A scan may be taken at a predetermined frequency, such as, for example, every second, or several times a second.

The particular scan frequency selected may vary in accordance with an embodiment. An embodiment may select a scan frequency that varies with the average expected peak width and may be, for example, an order of magnitude greater than this. In one embodiment, the mass spectrometer scans at a rate which is 10-fold higher than the rate at which compounds are eluting. This translates to at least 10 scans over an average chromatographic peak.

Figure 5:
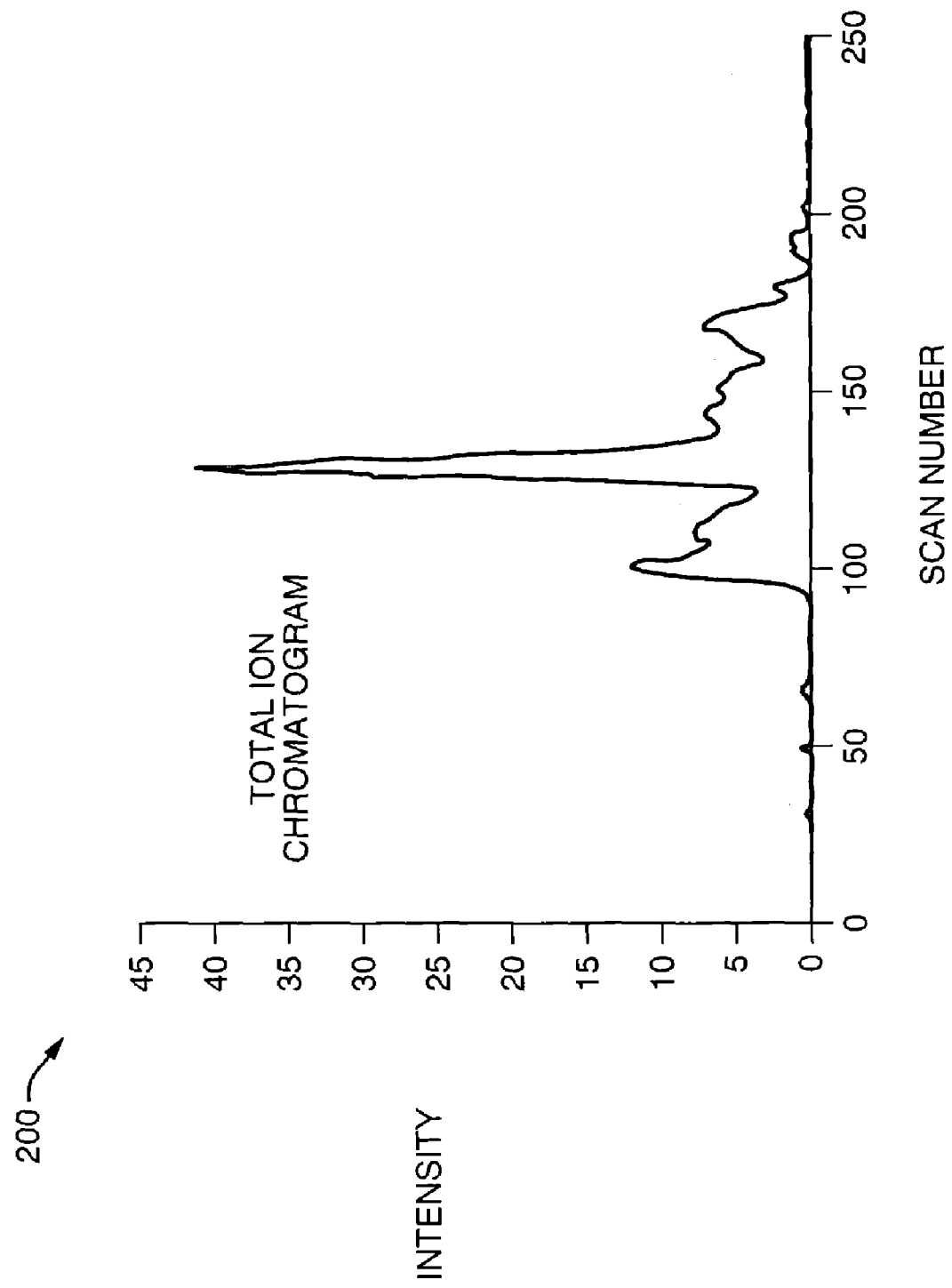
FIGS. 5-9 are example graphical illustrations of alternate displays of data output from the mass spectrometer of FIG. 4.

Referring now to FIG. 5, shown is one form of a graphical representation of the spectral data as may be displayed. Graphical display 200 of FIG. 5 shows a total ion chromatogram (TIC). The TIC represents the intensities of all the ions as summed in connection with each particular scan. Thus, the TIC represents an aggregate amount of ion intensity in each scan.

Figure 6:
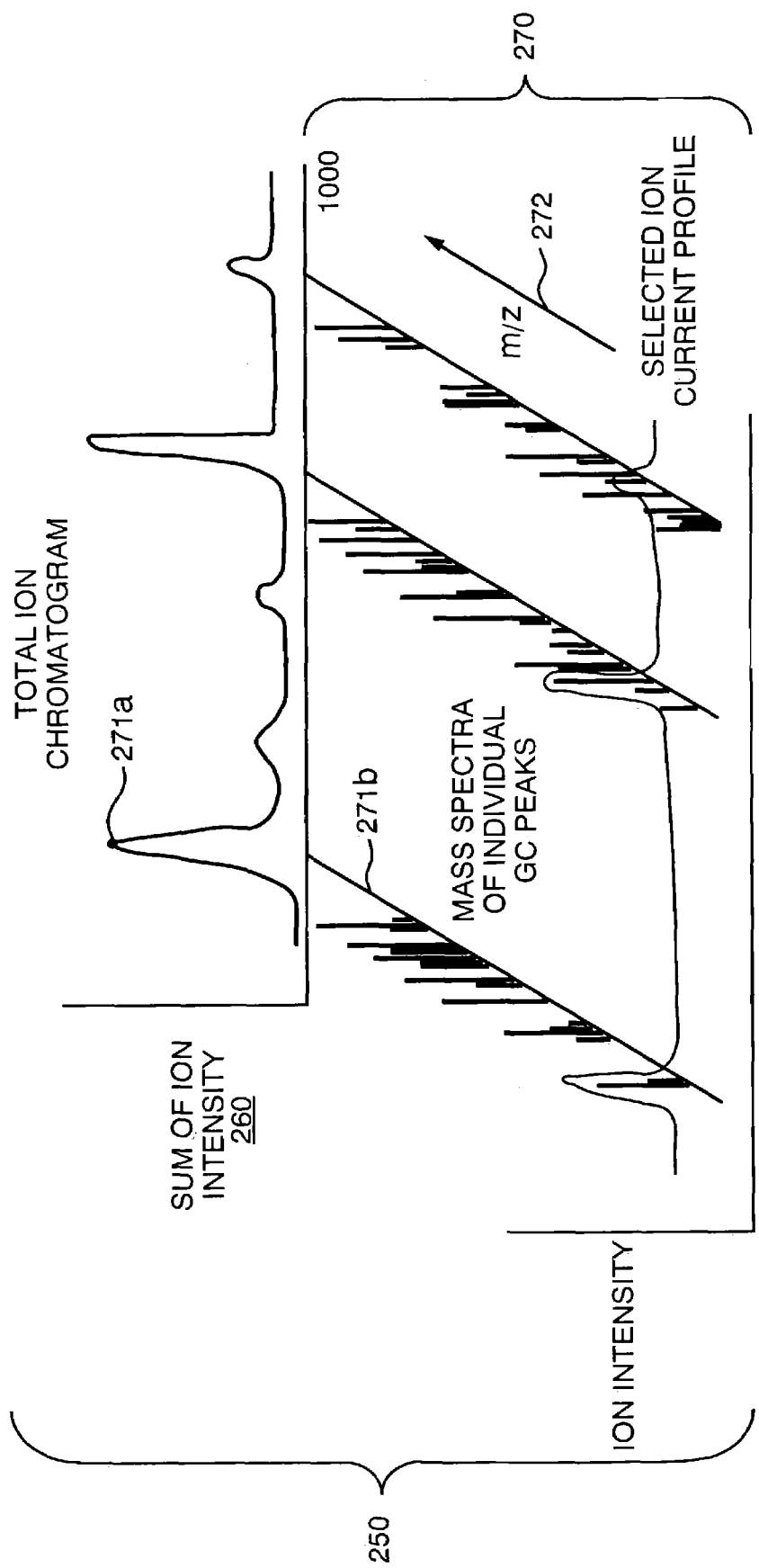

Referring now to FIG. 6, shown is an example of a graphical representation 250 of how a TIC 260 may further be represented by a plurality of individual ion profiles 270. A particular point 271a in the TIC 260 may be represented by summing the individual ion profiles 271b as illustrated in 270 along the direction indicated by arrow 272. FIG. 6 shows alternative data displays of chromatographic data as may be output from the mass spectrometer 18.

It should be noted that in connection with capturing spectra at a particular frequency, the particular frequency may vary in according with each embodiment. For example, with techniques described herein, spectra may be gathered several times every second. It should be noted that TICs are effected by noise components of the data set.

Figure 7:
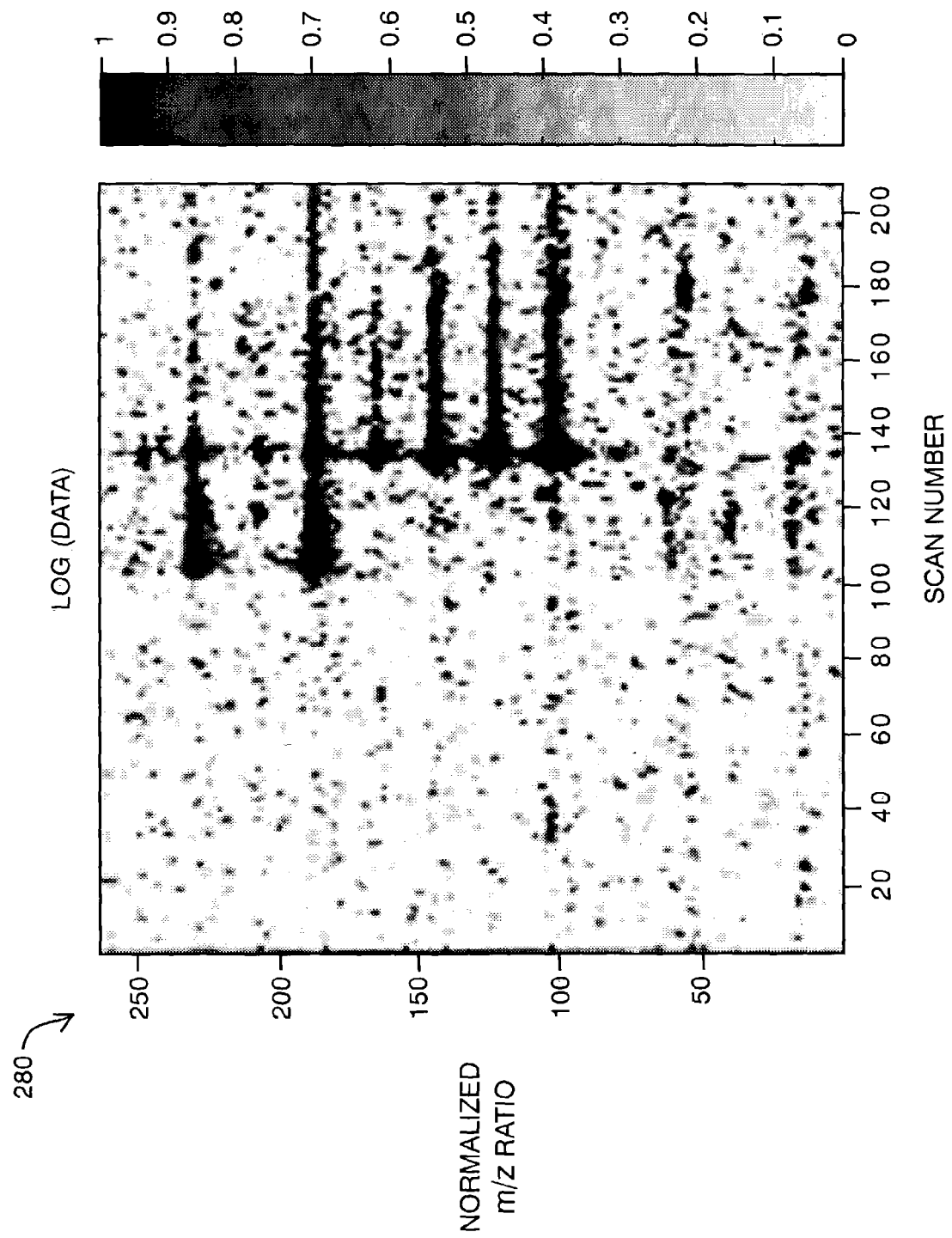

Referring now to FIG. 7, shown is an example of another form of how data output from a mass spectrometer may be displayed. The data display 280 may be referred to as a contour plot where the scan number is on the x axis. The particular m/z value is represented on the y axis with the intensity represented as a gray scale value. Viewing a slice vertically through the representation 280 of FIG. 7 results in a spectrum for a particular elution time. A horizontal slice of the graphical illustration 280 of FIG. 7 represents the ion current for a particular m/z value over time which is commonly referred to as the extracted ion chromatogram (XIC).

Figure 8:
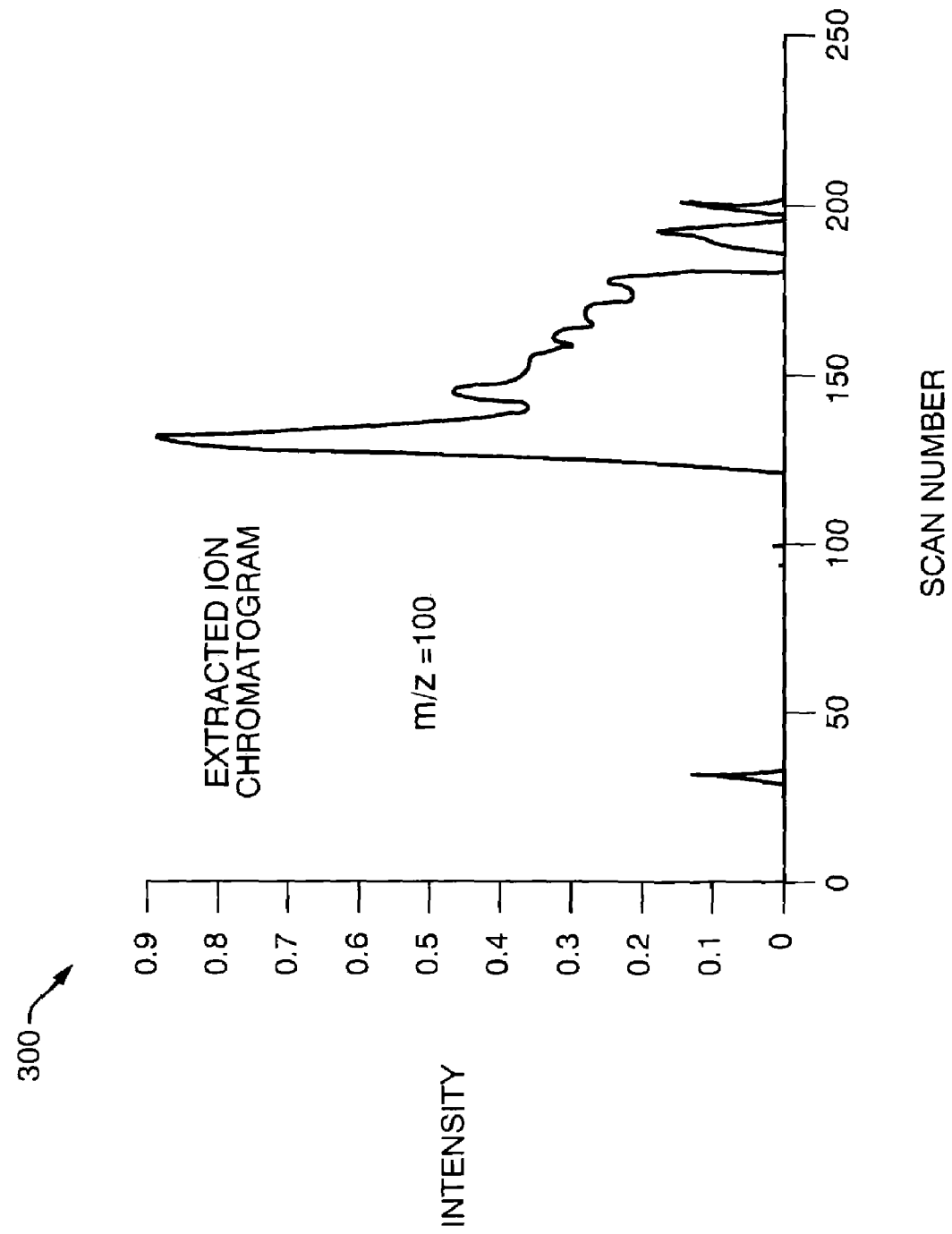

Referring now to FIG. 8, shown is an example of the graphical representation 300 of an XIC. The illustration 300 represents an XIC for an m/z ratio of 100 over time.

In connection with the XICs, it may be noted that two or more components of an original mixture may co-elute at a particular point in time. However, the elution profiles of each of the respective two components in most cases will exhibit differences over a series of time points or scans. It should also be noted that ions resulting from the processes of the mass spectrometer may tend to co-vary chromatographically by exhibiting similar elution profiles.

Figure 9:
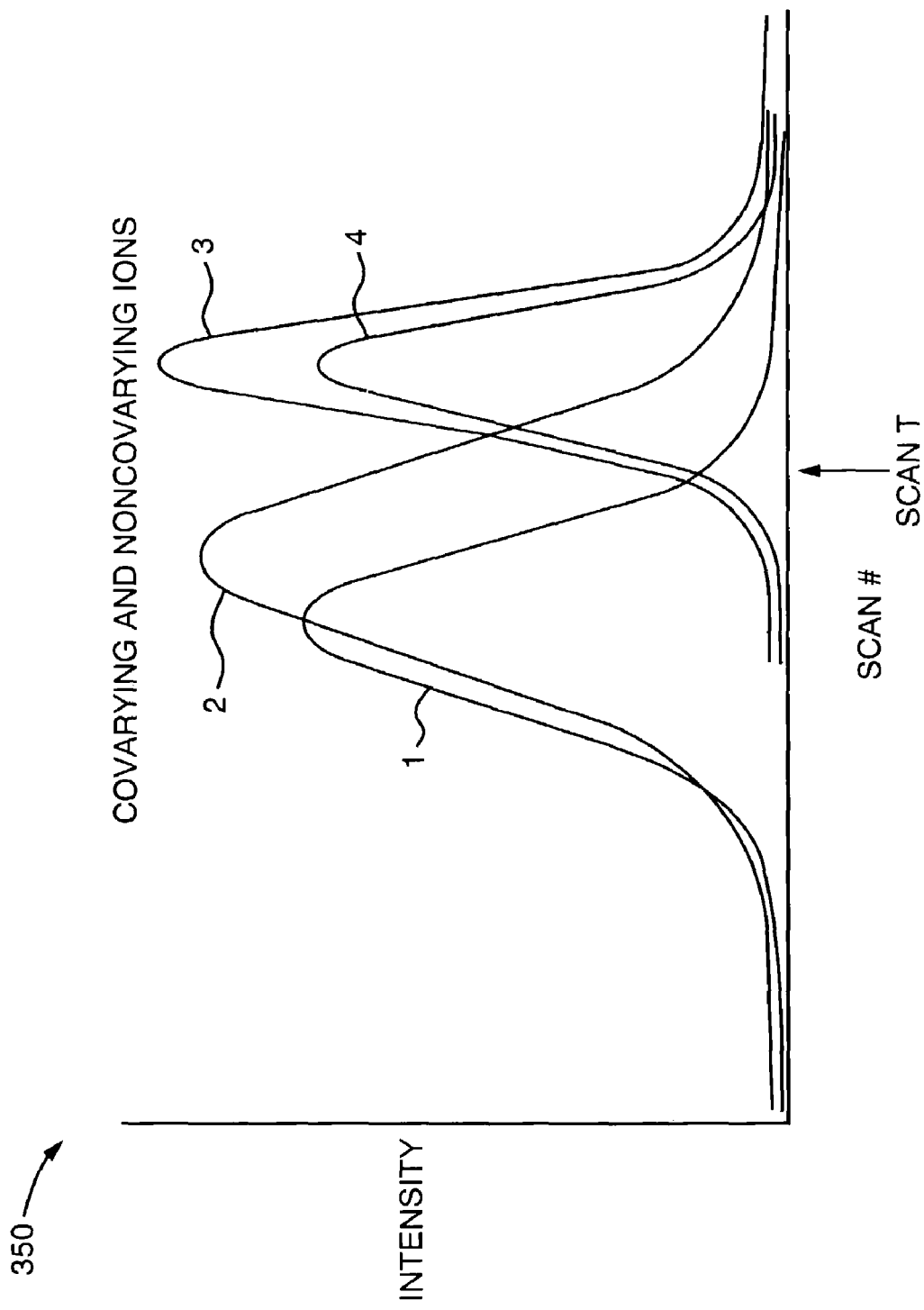

Referring now to FIG. 9, shown is an example of a graphical illustration 350 representing XICs for four different m/z values overlaid. All four m/z values are co-eluting at a scan point T as identified on the illustration 350. However, note that only ions 3 and 4 are co-varying. Co-varying ions in this example may be visible in a contour plot as shown in FIG. 7 as a series of horizontal bars arranged in a column. However, when the XICs of the corresponding ions 3 and 4 are examined, similarity in elution profiles may be observed. These observations regarding covariance may be utilized in the processing steps described herein.

Figure 10:
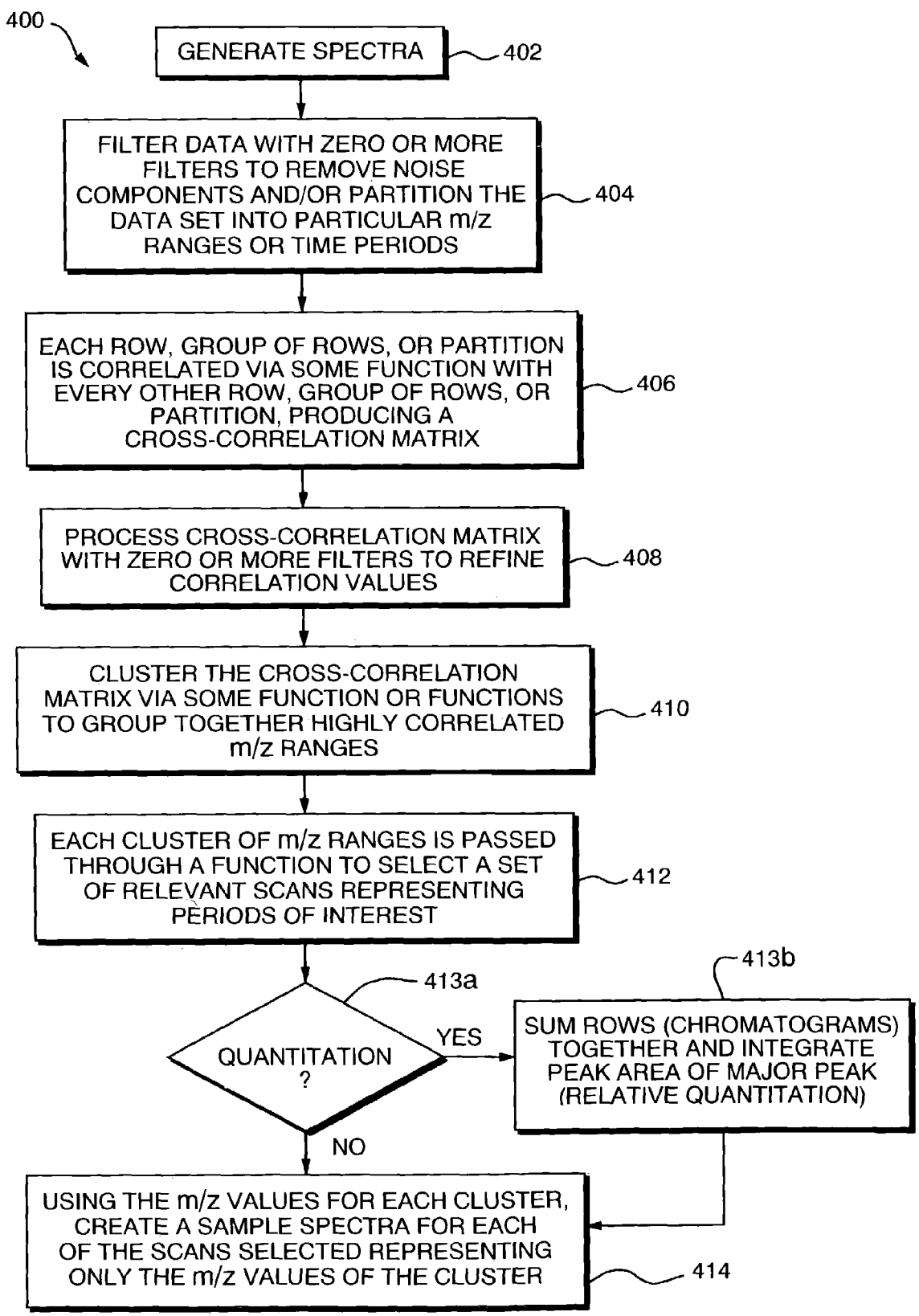
FIG. 10 is a flowchart of method steps of an example embodiment for performing ion identification and filter processing upon data output from the mass spectrometer of FIG. 4.

Referring now to FIG. 10, shown is a flowchart of processing steps that may be included in an embodiment of the ion identification and filter processing 24 previously described in connection with FIG. 1. At step 402, the spectra are generated as a result of mass spectrometer processing, for example, an LC/MS data set of a time series of spectra. The data set may be represented as three columns of data including a scan number, an m/z value, and a corresponding intensity. This may be as represented in example display 280 of FIG. 7. The s input data may also be represented as one or more XICs described elsewhere herein in which each m/z value is monitored over time. Each XIC is the scan number or time on the x axis with the intensity monitored over time on the y-axis. There is an XIC for each m/z value. The format of the data used in connection with the processing steps described herein is a two-dimensional matrix having a row index on the Y axis of the m/z ratio, and a column index on the X axis of a scan number. The value within a cell or entry identified by a row and column is the associated intensity value.

At step 404, the data may be filtered with zero or more filters to remove noise components and/or partition the data set into particular m/z ranges or time periods. It should be noted that in order to reduce the "noise" in the data set being analyzed, the choice of filters and the particular combination and order used may vary depending on the quality of the data. For example, in one embodiment, the following filtering techniques may be used:
1. truncate data below a certain threshold
2. median filter
3. 2-D gaussian convolution filter
4. remove DC noise using DC filtering techniques
   These and other filtering techniques may be found, for example, in Pratt, W. K., entitled "Digital Image Processing", by John Wiley & Sons, 1991, New York.

Using the foregoing types of filtering techniques in one example embodiment, the output of the filtering processing of step 404 is a data matrix with the same number of columns (scans or time points) as the original matrix. An embodiment may have a reduced number of rows as a result of step 404 processing in comparison to the number of rows in the original data set due to removal of the zero rows generated by filtering of noise. The magnitude of the data reduction depends on the cutoff threshold in step 1 above, as well as other filter parameters used in connection with steps 2-4 processing that may be utilized in an embodiment. In one embodiment in connection with steps 1-4 as outlined above, the foregoing parameters may be used with associated processing steps: step 1) truncate values less than 5% of maximum, step 2) 5×5 median filter, and step 3) use a Gaussian filter with a width approximately that of the expected width of the chromatographic peaks. In connection with filtering step 4 denoted above, no parameter selection is necessary. It should be noted that the foregoing techniques, as well as guidelines for their use, are well known.

An embodiment may use any combination of hardware and/or software to implement the foregoing filtering processing in an embodiment. In an embodiment using software to implement the foregoing filtering steps and other processing described herein, any one or more programming languages, such as, for example, C, C++, Java, FOTRAN, and/or any one or more software packages, such as, for example, MATLAB, may be used. The particular ones may vary in accordance with what is available in each implementation.

As an alternative, or in addition, to filter processing at step 404, an embodiment may partition the data set to reduce the number of rows in the data matrix One embodiment may select only those rows of data within a particular m/z range. For example, data peaks may be determined and a particular m/z range may be selected for a range of values on spanning a data peak. Use of partitioning in this processing step refers to a process of data reduction. At some point, partitioning may become necessary in an embodiment because of memory constraints due to the size of the resultant correlation matrix formed and used in other processing steps described elsewhere herein. The size of the correlation matrix depends on the number of rows in the original data matrix (number of non-zero mass samples). Consider, for example, an embodiment performing the processing steps described herein in connection with flowchart 400 using time of flight (TOF) datasets having greater than 100,000 mass samples for each spectrum in the dataset. If all m/z rows of the data set are considered, assuming that there is no truncation or filtering, then the correlation matrix has 1e10 elements, which at 4 bytes an element, results in a 39 GB matrix. An embodiment may utilize the partitioning technique to reduce the size of the matrix.

Figure 13:
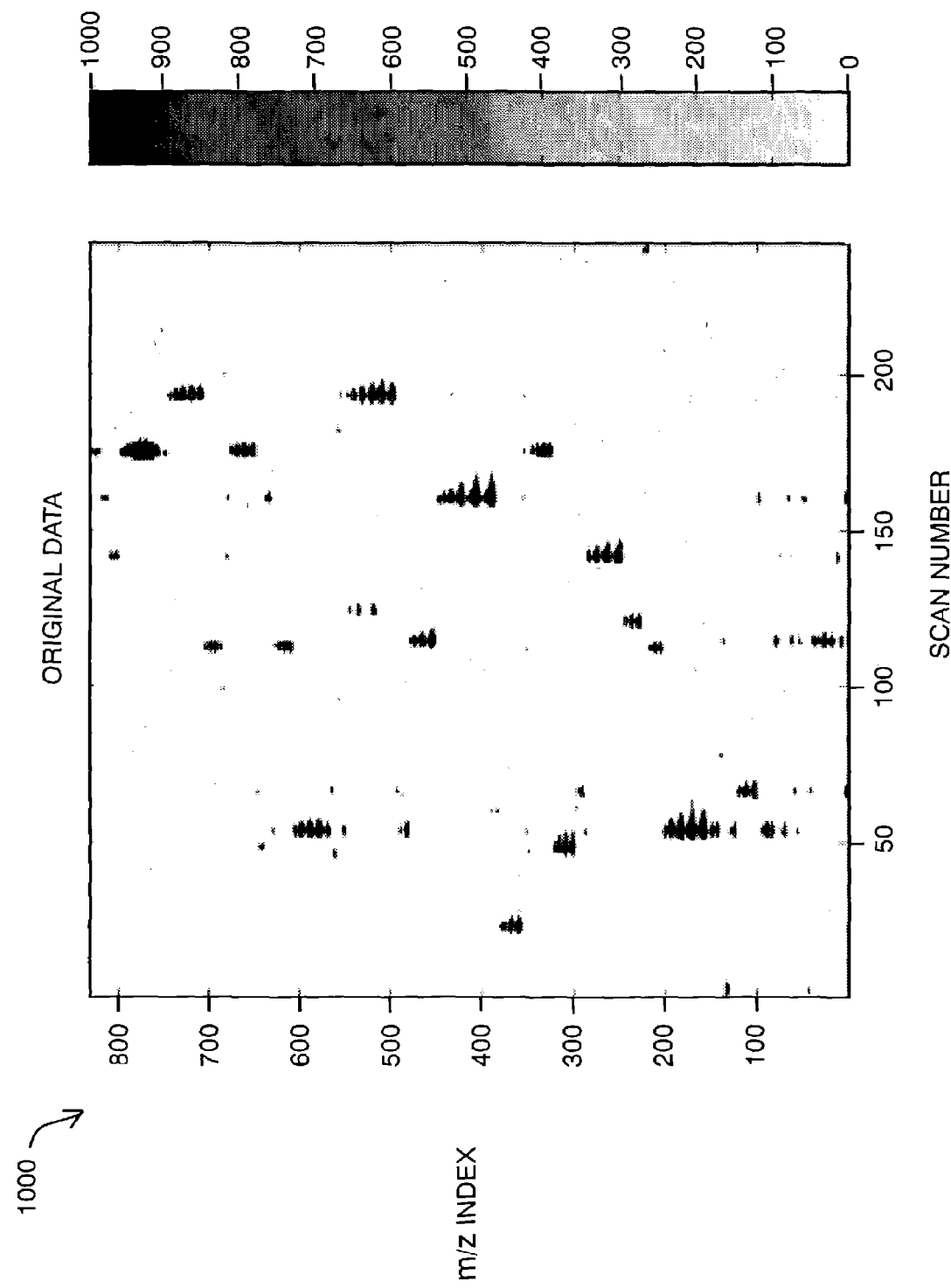
FIGS. 13-17 are example graphical illustrations of data sets at various processing steps of the method of FIG. 11.
Figure 14:
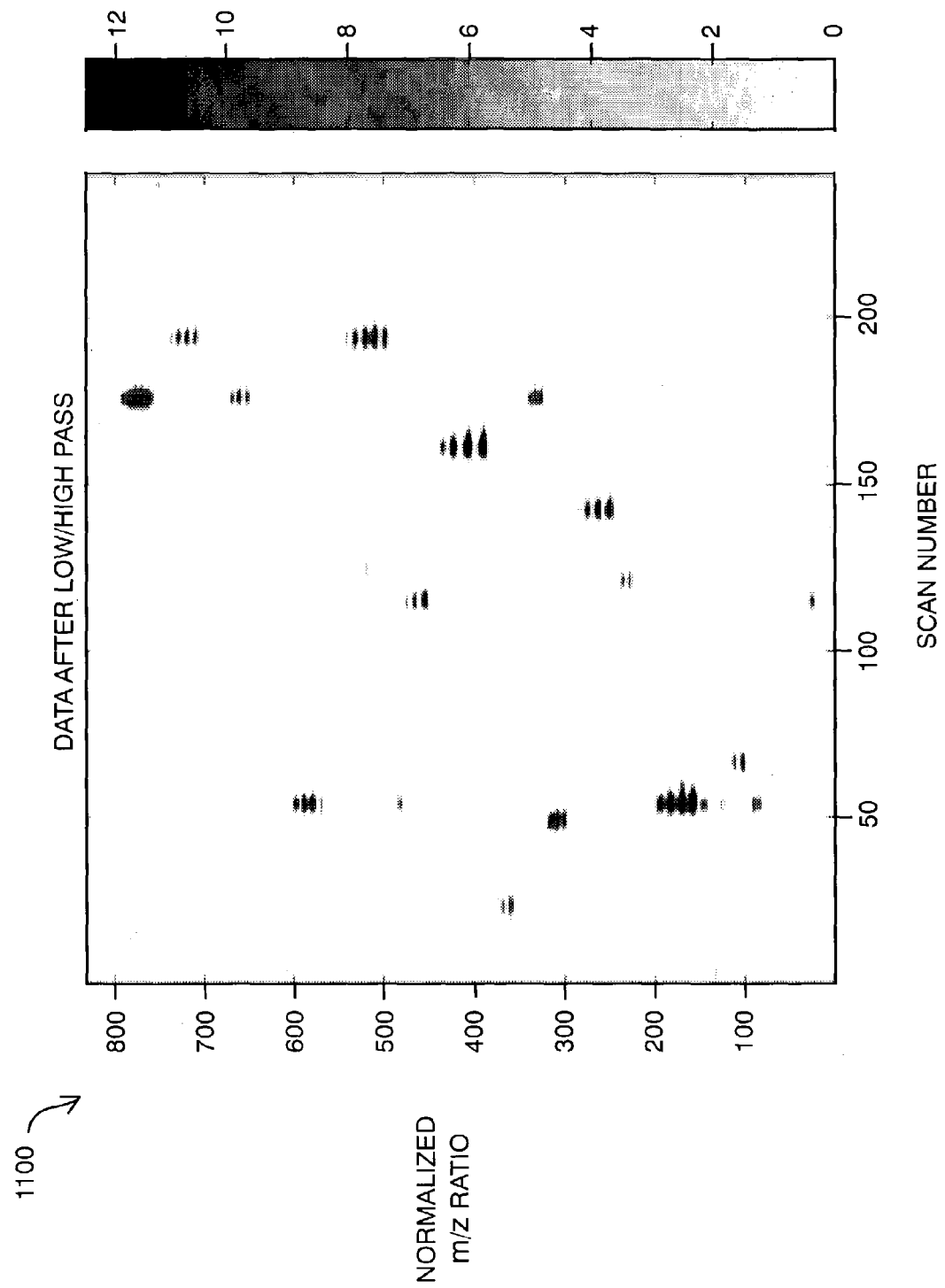
Figure 15:
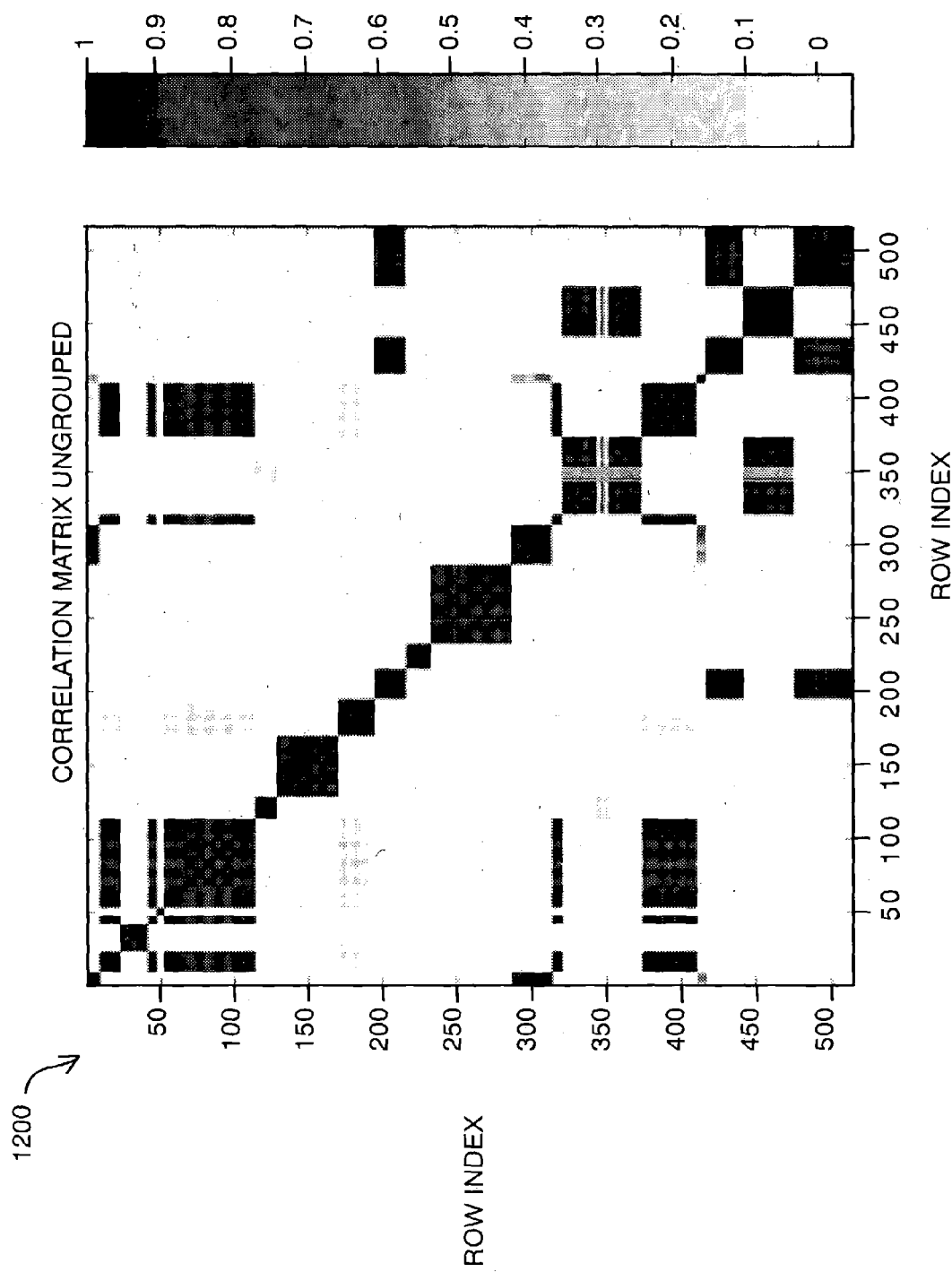
Figure 16:
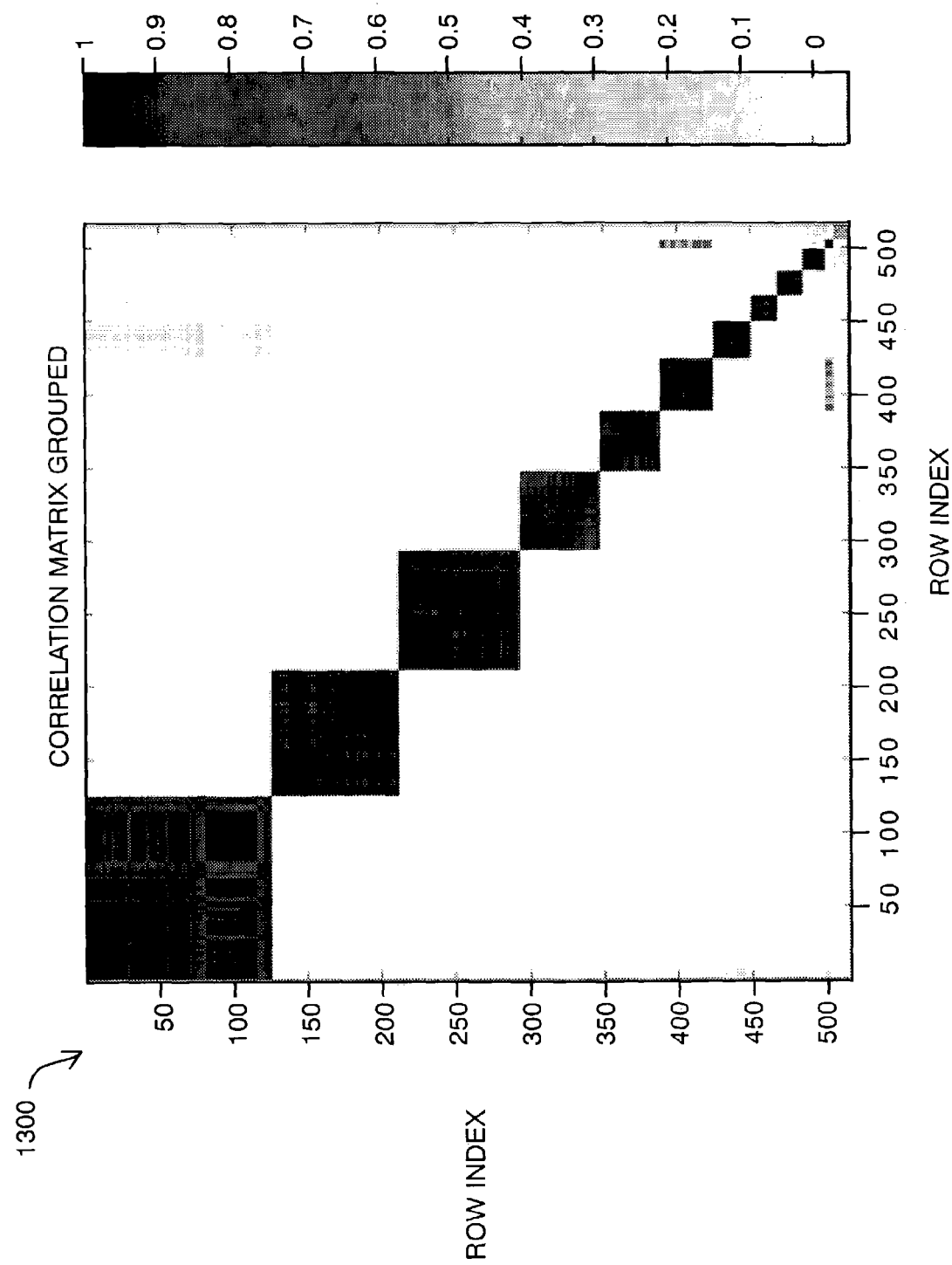

Referring back to FIG. 7, graph 280 may be represented by a data set in matrix form, for example, having approximately 250 m/z rows in the dataset represented. Actual datasets tend to be much larger, but this serves as a good example. Referring to the graph 280, 6 major peaks may be discerned. A peak finding routine may be utilized to locate the major peaks with reference to a particular scan number. One peak finding technique that may be used in an embodiment is based on the calculation of derivatives. For example, at the peak maximum, the first derivative is zero and the second derivative is negative. The peak finding routine may be performed in the time and m/z dimension to find the peaks. A range of scans may be selected, peak+/− range value, as well as examining only scans for the maxima. The multiple rows in each peak may be reduced by, for example, combining the rows by adding them. An embodiment may also take the median of samples. An embodiment may also select the maximum representative row for the mass peak. Another embodiment may include the use of image processing algorithms, such as the watershed algorithm, to perform peak finding in the time and m/z dimensions simultaneously. The watershed algorithm, as well as other image processing techniques are known in the art and described, for example, in K. R. Castleman, "Digital Image Processing" Prentice-Hall Inc., New Jersey 1996. In this embodiment using the watershed algorithm, the dataset is treated as an image, for example, as shown in FIG. 13. First, the local maxima are determined using an extended-minima transform and imposed on the image as described, for example, in Pierre Soille, Morphological Image Analysis: Principles and Applications, Springer-Verlag, 1999, pp. 170-171. This helps reduce oversegmentation during subsequent processing steps. Next, watershed segmentation is performed on the image which detects the peak boundaries (in time and mass) and segments peaks which are not fully resolved. Using the foregoing has several advantages. The peaks, which consist of multiple mass rows or chromatograms, may be combined into a single peak chromatogram by summing all of the intensities within the peak boundary in a row-wise manner. The peak chromatograms may then serve as an inputs to the grouping algorithm, rather than using every mass row in the dataset. This results in a significant reduction in the number of rows input to the grouping algorithm, and a smaller size of the resultant correlation matrix. Additionally, peak splitting is no longer neccessary with this technique, since the peak detection performs this automatically. Furthermore, quantitation may be performed by summing the intensities within the peak boundaries.

Using any one of the foregoing results in collapsing the multiple rows into one peak. It should be noted that different techniques used here may effect subsequent processing steps. For example, if rows are added together, the processing at step 414 in FIG. 10 is also affected. Without such peak finding routines, multiple rows of data are used for a single peak in a data matrix as input into a correlation routine, which is redundant due to the high correlation of rows within a single peak. Referring back to the example dataset with 250 rows, this may be reduced to a matrix of 6-10 rows, corresponding to the number of peaks, and reduces the size of the correlation matrix as well.

It should be noted that the partitioning may be preferred to filtering for a large data set, for example, greater than 10,000 m/z samples, due to the computer resources and time required for performing processing of the large data sets.

At step 406, each row, group of rows, or partition is correlated using some function with every other row, group of rows, or partition producing a correlation matrix representing the degree to which the rows are related to one another. Each row represents intensities over time for a particular m/z range. The resulting correlation matrix is a two dimensional matrix symmetrical about the diagonal such that the diagonal entries are 1 and the upper and lower triangular portions are identical. In other words, each entry having indices "i,j" is the same value in the entry having indices "j,i". The correlation for two rows x and y may be represented as:

$$r = \frac{\sum_{i=1}^{n} xi - mx * yi - my}{\sqrt{\sum_{i=1}^{n}(xi-mx)^2} \sqrt{\sum_{i=1}^{n}(yi-my)^2}}$$

in which "mx" represents the mean value of row x, "my" represents the mean value of row y, and the index "i" ranging from 1 to n represents the index of the entry in the row with n being the total number of rows. At step 408, the correlation matrix is processed with zero or more filters to further refine the correlation values. At step 410, the cross correlation matrix may be clustered using some function or functions to group together highly correlated m/z ranges or identify clusters of m/z ranges. One particular clustering or grouping technique is described elsewhere herein in more detail. An embodiment may also utilize other clustering or grouping techniques such as, for example, hierarchical clustering, K—means clustering and others. Such techniques are described, for example, in Seber, G. A. F., Multivariate Observations, Wiley, N.Y., 1984, and Spath, H., Cluster Dissection and Analysis: Theory, FORTRAN Programs, Examples, translated by J. Goldschmidt, Halsted Press, New York, 1985.

At step 412, each cluster or group of m/z ranges is passed through a function to select a set of relevant scans representing periods of interest. In one embodiment, the one or more scans may be determined by first determining a maximum point by summing the intensities of the XICs at each scan point within each group, for example, by adding the rows of the data set for all rows within each group. The scan corresponding to the maximum point or peak intensity may be determined as a scan of interest. An embodiment may also determine more than one scan of interest by determining a scan range, for example, utilizing the peak or maximum value. The scans of interest selected may be those scans falling within peak+/- range value, where range value may vary with an embodiment. The range value may be, for example, ½ the peak value.

One technique for selecting the range of a chromatographic peaks is to select the range that is full width at half maximum (FWHM), meaning that one selects the range between the two points on either side of the peak that are at half the height of the peak. Other embodiments may use other techniques for range determination.

As described herein, the scan(s) of interest may vary with embodiment. An embodiment may determine a single point as a scan of interest representing, for example, the maximum average ion signal for the selected m/z values or the time centroid of the cluster. An embodiment may select a range of scans, such as the complete set of scans containing a signal for selected m/z values, and the like. More than one scan may be selected, for example, if the signal is weak and/or there is excessive noise to increase the signal to noise ratio. One technique sums all columns containing a signal for the group to maximize the signal.

Control proceeds to step 413*a* where a determination is made as to whether quantitation is being performed. Quantitation generally refers to the processing step of determining an amount or quantity of molecule rather than identifying a particular type or types of molecules. If quantitation is being performed, control proceeds to step 413*b* where rows (chromatograms) are added together. Relative quantitation is performed by integration of a chromatographic peak to obtain the peak area, which is proportional to the quantity of the component in the mixture. The foregoing integration sums the intensities for a given m/z range between two time points spanning the peak of interest.

At step 414, the m/z value(s) for each cluster or group as included in the input data set may be used to create a sampled spectrum for each of the scans selected in step 412 representing only the m/z values of the cluster. In other words, for each one or more scan values of interest, a corresponding column of intensities from the original data set is used to produce a spectrum for each group. It should be noted that when performing step 414 processing, an embodiment may utilize the original data set or a filtered form of the original data set to produce the resulting spectra.

The input data produced at step 402 used in the foregoing processing may be gathered by running the mass spectrometer at normal energy levels (U spectrum), high fragmentation energy levels (F spectrum), or in alternating scan mode producing alternating U and F spectra. When using alternating scan mode producing data sets including alternating U and F spectra, the chromatographic correlation of the parent peptides (U spectra) and their respective fragment ions (F spectra) may be used to associate parents with their fragments. This characteristic of time or scan correlation between parents and associated fragments may be used, for example, in cases where multiple parents are being fragmented simultaneously, but exhibit sufficient differences in their respective elution profiles. The respective differences in the elution profile enable differentiation between the different parents to be matched with appropriate fragments.

If the input data is produced using the alternating scan mode, two different approaches may be used in processing the input data. Both approaches are described in following paragraphs. In a first approach, the U and F spectra may be combined. In a second alternate approach, the U and F spectra may be processed separately.

For the first approach, the U and corresponding F spectral pairs are added together prior to performing step 406. It should be noted that the F spectrum may be filtered prior to performing the summation of the F and corresponding U spectrum. This filtering may be performed, for example, due to the lower intensity of fragmentation spectra. In one embodiment, a combination of baseline subtraction, Kalman smoothing and Savitzky-Golay filtering are performed. Subsequent to performing the summation, additional filtering may also be performed on the composite spectra. Correlation, filtering, clustering, selection of relevant scans and other processing associated with steps 406, 408, 410, and 412 then proceed as described elsewhere herein resulting in a set of component spectra (U and F combined). In following paragraphs, this may be referred to as the A set. When performing processing associated with step 414, two different spectra are created—one from the original U spectrum at a selected scan for a group, and a second F spectrum sampled at the same scan.

In the first approach, the precursor (parent) ions may be identified by first deriving the A set spectra representing the combined U and F, and then sampling the original U-only dataset at the masses present in set A, and at the scan maximum identified for set A. The parent ions are where there are intensities at the sampled masses in the U-only spectra.

The combined spectra in the A set, assuming that no parents have exactly the same chromatographic profiles, should contain the parent's m/z value with fragments from only that parent. The next step is to determine which m/z value in this A spectrum is the parent. The m/z values identified in the A spectrum are then used to sample the original U spectra at the scan maximum identified for spectrum A. Intensities occurring at these sampled masses in the U spectrum indicate the parent ion masses. Absence of signal at a sampled m/z indicates a fragment ion. By performing the foregoing, the parent masses are identified within the combined U-F component spectrum, spectrum A.

In addition to the first summation approach, a second time correlation approach may be utilized. Correlation processing of step 406 may be performed on the U and F datasets separately. The U and F spectra may be sampled at the scan values as described above in alternating mode. It should be noted that to utilize this second approach, the F spectra should have a sufficient signal to noise ratio for satisfactory correlation. If this is not the case, the summation technique may perform better. Additionally, as with the summation method, filtering techniques may be performed on each of the F and/or U spectra. It should be noted that different filtering techniques may be utilized in an embodiment on the F spectra due to the typical lower signal to noise ratio making the F spectra more error sensitive. As in the summation method, there should be a 1-1 correspondence between the spectra in both the U and F sets, the parents in the sets from the U, and the fragments in the sets from F, correlated in time.

Figure 11:
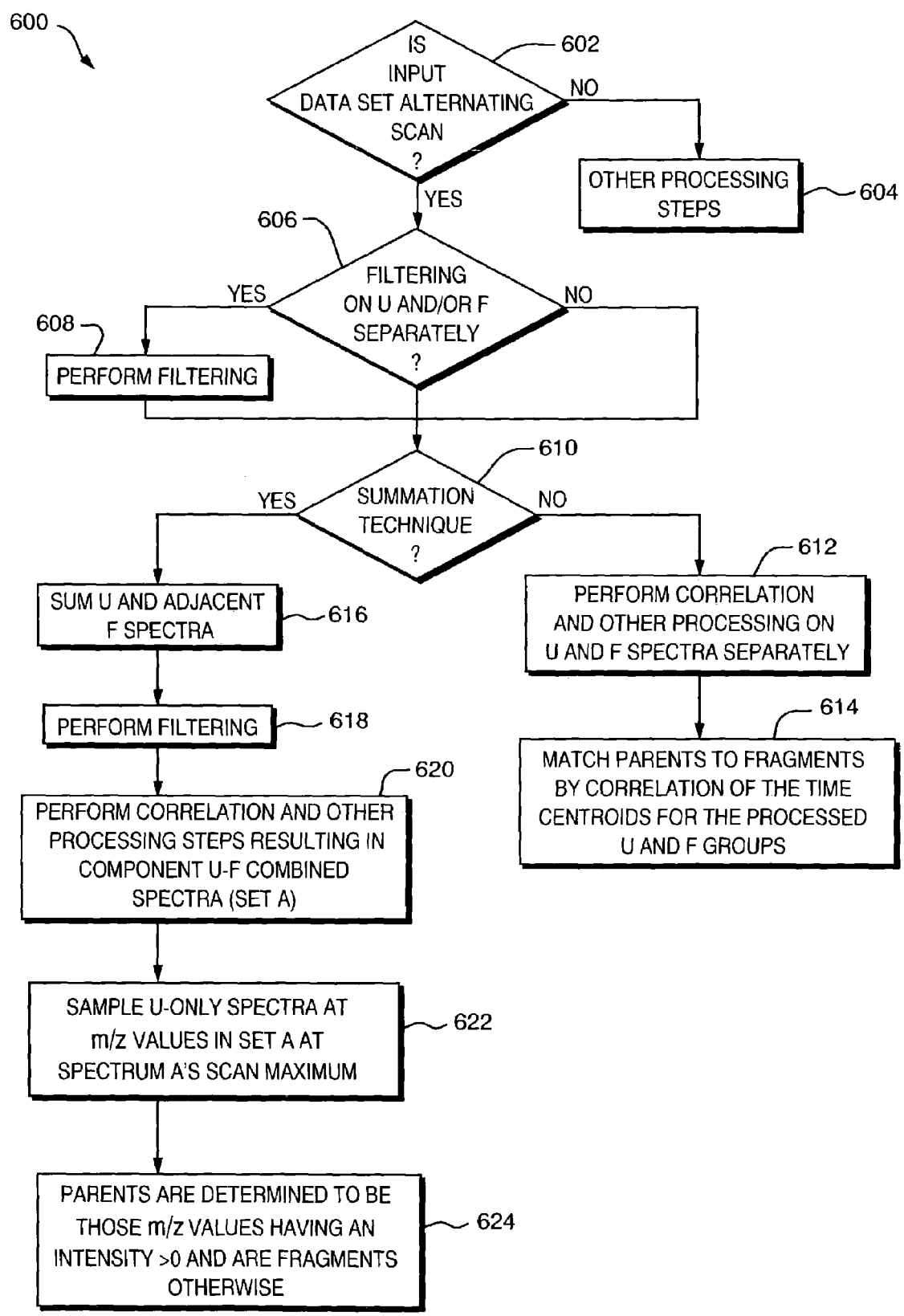
FIG. 11 is a flowchart of method steps of an example embodiment for processing different types of mass spectral data sets.

Referring now to FIG. 11, shown is a flowchart 600 of method steps of one embodiment for performing processing of input spectra produced using a mass spectrometer operating in alternating scan mode. Flowchart 600 summarizes the processing steps described above.

At step 602, a determination is made as to whether the input data set includes alternating U and F spectra. If not, control proceeds to step 604 where the processing steps described in connection with flowchart 400 may be performed to process the input data set. Otherwise, control proceeds to step 606 where determination is made as to whether any filtering is performed upon the separate U and/or F spectra. If so, control proceeds to step 608 where the filtering is performed prior to step 610. At step 610, a determination is made as to whether the summation technique, the first approach described above, is to be performed. If so, control proceeds to step 616 where U and adjacent F spectra are added together. At step 618, filtering may be optionally performed on the combined U-F spectra. At step 620, the correlation and other processing steps, such as 406, 408, 410, 412 and 414 described in flowchart 400, are performed producing a resultant combined U-F spectra referred to as set A. At step 622, the m/z values identified in the A spectrum are then used to sample the original U spectra at the scan maximum identified for the spectrum in set A. At step 624, parent ion m/z values are determined to be those having an intensity value>0. Absence of a signal at a sampled m/z value such that the intensity=0, indicates a fragment ion.

If at step 610 it is determined that the summation technique is not used, the alternative second approach, the time correlation approach, is utilized. At step 612, correlation and other processing steps, such as 406, 408, 410, 412 and 414 described in flowchart 400, are performed separately on the U and F spectra. At step 614, the parents are matched to corresponding fragments utilizing the correlation of time centroids for the processed U and F groups.

It should be noted that the mass spectrometer in alternating scan mode may utilize a scan rate that is much higher than the rate at which components are eluting. For example, in one embodiment, the scanning rate is a factor of 10 or more than the rate at which components are eluting from the mass spectrometer. Selected scanning rates are described elsewhere herein.

If the input data set includes only U spectra with no fragments, the analysis is performed to examine each peptide in the mixture, or molecule in the sample. Each group corresponds to the charge states and isotopes of a single peptide or molecule coeluting at the same time. When the input data set includes only U spectra, the techniques described herein may be used to determine which m/z ratios of peaks are of the same peptide or molecule. This may be a useful preprocessing step prior to performing, for example, charge assignment, isotope clustering, de novo sequencing, database searching, and the like.

If the input data set includes only F spectra, each group corresponds to the charge states, isotopes, and fragments of a single peptide or molecule coeluting at the same time.

Figure 12:
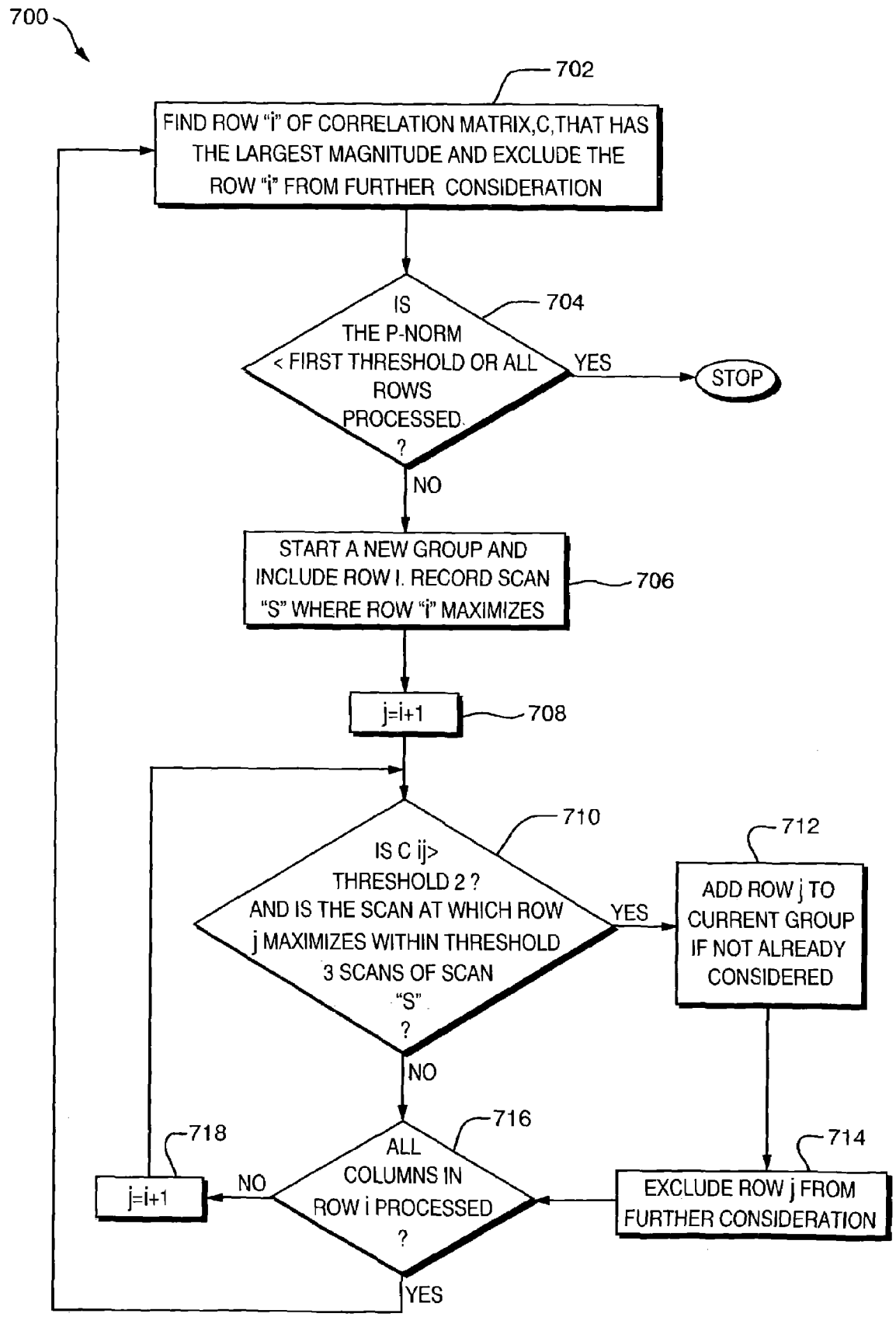
FIG. 12 is a flowchart of method steps of an example embodiment for performing clustering or grouping of highly correlated rows as used in FIG. 12 flowchart processing steps.

Referring now to FIG. 12, shown is a flowchart 700 of method steps of an example embodiment of a clustering or grouping process. The method steps of flowchart 700 may be performed as part of step 410 processing. The input at step 702 is the correlation matrix, C, produced as a result of step 406 processing. At step 702, the row "i" of the matrix C is determined as the row with the largest magnitude. The magnitude of a vector may be defined in different ways. For example, in one embodiment, the magnitude may be defined as a p-norm of a vector for 1<=p<=infinity, p being an integer value, for a vector $x_1$ as:

$$\|x\|_p = \left[\sum_{j=1}^{n} |x_j|^p\right]^{\frac{1}{p}}$$

The vector x may include "n" values that are each real or complex elements. In the instance where p=infinity, the following is true:

$$\|x\|_\infty = \max_{1 \le j \le n} |x_j|$$

An embodiment may also use other types of norms in determining a magnitude, such as, for example, other norms involving derivatives, such as the Sobelev norm. Other measures of magnitude that may be included in an embodiment include: a number of elements above a threshold, entropy, concentration, logarithm of energy, and the like as described in, for example, Wickhauser, "Adapted Wavelet Analysis from Theory to Software", 1994, A. K. Peters, Massachuetts, and Atkinson, "An Introduction to Numerical Analysis", 1989, John Wiley and Sons, USA.

At step 704, a determination is made as to whether the magnitude is less than a first threshold, or if all rows have been processed. If either condition is true, processing stops. Otherwise, control proceeds to step 706 where a new group is started with the selected row "i" included in the new group. Scan "S" at which row "i" maximizes is also determined and used as a criteria for grouping subsequent rows. The first threshold may vary with each embodiment and may be empirically determined in accordance with each particular data set and mass spectrometer settings and characteristics. For example, in one embodiment the first threshold may be 0.15 specifying a minimum correlation value. If this first threshold is increased, the number of groups may decrease. At step 708, a counter "j" is initialized to be the value of "i+1". At step 710, a determination is made as to whether the current element, Cij is greater than a second threshold, and whether the peak of row "j" is within a certain number of scans (threshold 3) of scan "S" (peak scan for row "i"). For example, in one embodiment, this second threshold may be 0.75 and the third threshold=2 scans. If Cij is greater than the threshold 2, and the scan difference is less than threshold 3, control proceeds to step 712 where row j is added to the current group if the row j has not already been considered. At step 714, row j is excluded from further consideration and control proceeds to step 716. If, at step 710, it is determined that Cij is not greater than the second threshold, control proceeds directly to step 716.

It should be noted that the selection of the first threshold (threshold 1), as used at step 704, and the second threshold (threshold 2) as used in step 710 may be selected to improve the quality of the groupings of the rows and to minimize the number of ungrouped rows. Threshold 1 may be lowered to minimize the number of ungrouped rows, and threshold 2 may be increased to improve the quality of the grouping. Since selection of these two thresholds are interdependent, the value selected for one varies with the other in an embodiment. It should be noted that the selection of threshold 3 may vary with each embodiment and may be characterized as being data-dependent. For example, selection of threshold 3 may be made depending on the scanning resolution, i.e. how many scans are acquired across a chromatographic peak.

At step 716, a determination is made as to whether all the columns in row "i" have been processed. If not, control proceeds to step 718 where j is increased by 1 and control proceeds to step 710 to examine the next element in the current row. If all columns in row "i" have been processed, control proceeds to step 702 where the next row "i" is determined.

It should be noted that the first threshold described above in connection with step 704 may affect the number of rows of the correlation matrix which are not included in a group. The ungrouped rows may include, for example, noise, or individual peaks, so that raising the cutoff threshold 1 reduces the number of grouped rows and removes noise in the dataset prior to correlation. Using the example embodiment of clustering or grouping described in connection with FIG. 12, the first and second thresholds in the grouping or clustering processing affect the number of ungrouped rows. Threshold 1 and threshold 2 both vary between 0 and 1. The first threshold, threshold 1, is the threshold for choosing a row as having valid data, and the second threshold, threshold2, is the threshold for grouping one row with another. Threshold 3 is the maximum separation (in scans or seconds) allowed between a row's chromatographic peak and the seed row's chromatographic peak.

What will now be described is a simplified example in which the method steps described herein are performed utilizing an initial data set in matrix form. In the following example, it is assumed that there is no filtering performed in connection with steps 404 and 408. Additionally, note that the data set used herein is not a typical data set but a small sample matrix selected for illustrative purposes of utilizing the techniques described herein. The correlation step 406 and grouping or clustering step 410 are now performed using a data matrix B (8×8). Each row represents a mass chromatogram and each column represents a scan or time point.

$$B = \begin{matrix} 0 & 10.798 & 79.788 & 10.798 & 0 & 0 & 0 & 0 \\ 0 & 0 & 0 & 4.3821 & 99.736 & 4.3821 & 0 & 0 \\ 0 & 0 & 0 & 0 & 0 & 199.47 & 0 & 0 \\ 0 & 32.395 & 239.37 & 32.395 & 0 & 0 & 0 & 0 \\ 0 & 0 & 10.798 & 79.788 & 10.798 & 0 & 0 & 0 \\ 0 & 0 & 0 & 0 & 0 & 398.94 & 0 & 0 \\ 0 & 398.94 & 0 & 0 & 0 & 0 & 0 & 0 \\ 0 & 21.596 & 159.58 & 21.596 & 0 & 0 & 0 & 0 \end{matrix}$$

A correlation matrix (8×8), C, is created as a result of step 406 processing. The resulting matrix C is:

$$\begin{matrix} 1 & -0.19738 & -0.18584 & 1 & .082468 & -0.18584 & -0.027494 & 1 \\ -0.19738 & 1 & -0.10636 & -0.19738 & 0.0076672 & -0.10636 & -0.15713 & -.19738 \end{matrix}$$

-continued

| | | | | | | | |
|---|---|---|---|---|---|---|---|
| −0.18584 | −0.10636 | 1 | −0.18584 | −0.18584 | 1 | −0.14286 | −0.18584 |
| 1 | −0.19738 | −0.18584 | 1 | 0.082468 | −0.18584 | −0.027494 | 1 |
| 0.082468 | 0.0076672 | −0.18584 | 0.082468 | 1 | −0.18584 | −0.18584 | 0.082468 |
| −0.18584 | −0.10636 | 1 | −0.18584 | −0.18584 | 1 | −0.14286 | −0.18584 |
| −0.027494 | −0.15713 | −0.14286 | −0.027494 | −0.18584 | −0.14286 | 1 | −0.027494 |
| 1 | −0.19738 | −0.18584 | 1 | 0.082468 | −0.18584 | −0.027494 | 1 |

The grouping or clustering steps of flowchart 700 may be performed to group particular rows of the correlation matrix C together. A group index vector (group) having a number of entries equal to the number of rows in the correlation matrix may be used to indicate which rows in the correlation matrix belong to which groups. This indication may be made by having a group number in each entry and the n-th entry of the group index vector identifies the group number of the n-th row of the correlation matrix.

Continuing with the foregoing example, the associated group vector is:

group=1 0 2 1 0 2 0 1

To illustrate this further, the correlation matrix C1 may be reordered according to the labels in the associated group vector, in order demonstrate the nature of the grouping algorithm:

$$C1 = \begin{pmatrix} 1 & 1 & 1 & -0.18584 & -0.18584 & -0.027494 & -0.19738 & 0.082468 \\ 1 & 1 & 1 & -0.18584 & -0.18584 & -0.027494 & -0.19738 & 0.082468 \\ 1 & 1 & 1 & -0.18584 & -0.18584 & -0.027494 & -0.19738 & 0.082468 \\ -0.18584 & -0.18584 & -0.18584 & 1 & 1 & -0.14286 & -0.10636 & -0.18584 \\ -0.18584 & -0.18584 & -0.18584 & 1 & 1 & -0.14286 & -0.10636 & -0.18584 \\ -0.027494 & -0.027494 & -0.027494 & -0.14286 & -0.14286 & 1 & -0.15713 & -0.18584 \\ -0.19738 & -0.19738 & -0.19738 & -0.10636 & -0.10636 & -0.15713 & 1 & 0.0076672 \\ 0.082468 & 0.082468 & 0.082468 & -0.18584 & -0.18584 & -0.18584 & 0.0076672 & 1 \end{pmatrix}$$

Referring now to FIGS. 13-17, shown are example graphical displays of a data set at different points in processing when performing the method steps of FIG. 10. FIG. 13 shows a sample input data set 1000 that may be generated as a result of step 402 processing. After filtering at step 404, the original data set may be represented as in example display 1100 of FIG. 14. After the correlation processing step 406, the correlation matrix may be graphically represented as 1200 in FIG. 15. After identifying groups of clusters by performing the method steps of flowchart 700 of FIG. 11, the resulting groupings may be graphically illustrated by reordering the correlation matrix as in 1300 of FIG. 16. The filtered data may be grouped according to the group vector which results from performing the steps of flowchart 700.

Figure 17:
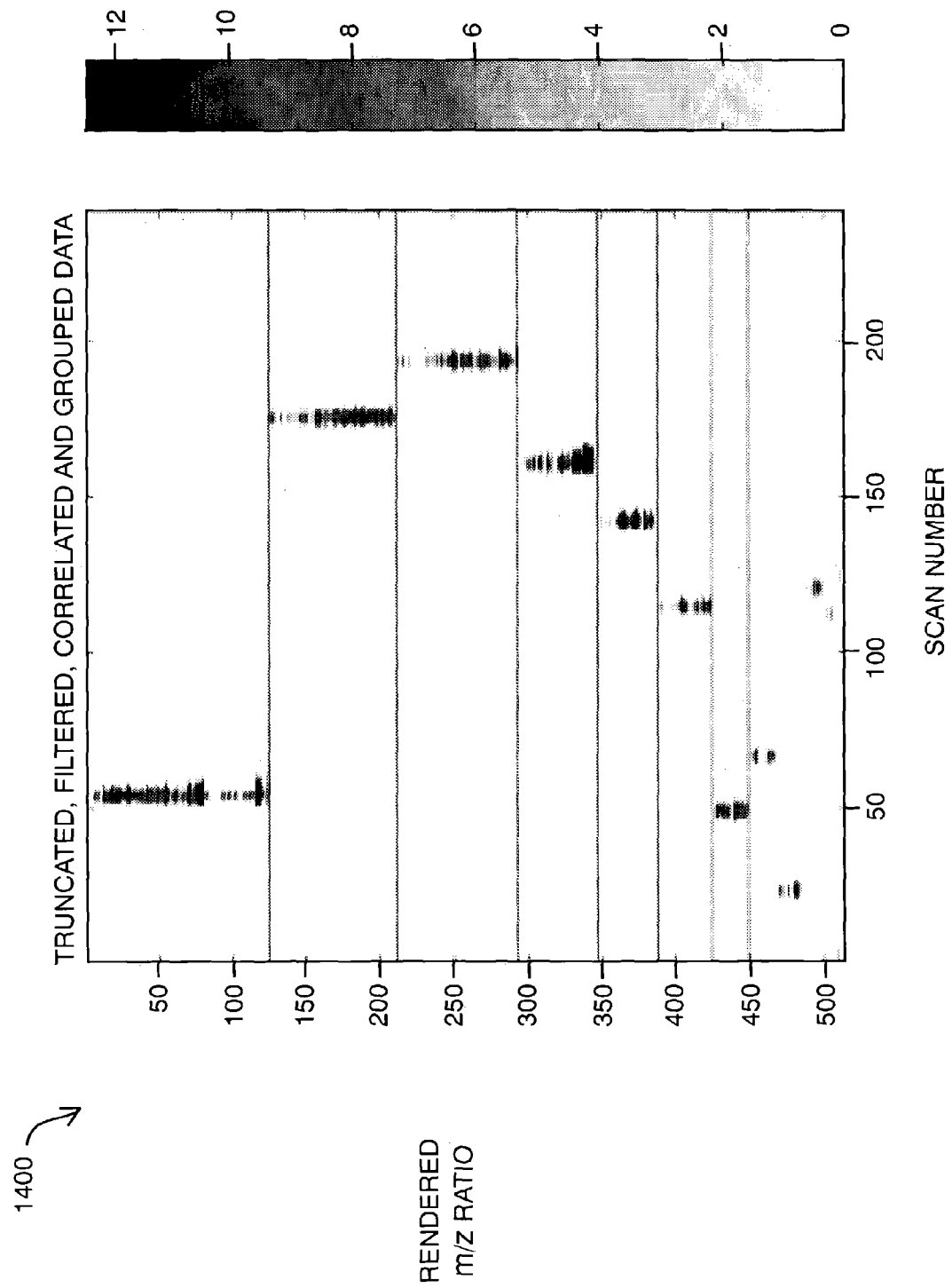

The example display 1400 of FIG. 17 represents the reordered m/z rows such that m/z rows in the same group are adjacent. After selecting relevant scan(s) for each group, the corresponding intensities for the selected scans may be obtained from the filtered data set to produce a resulting spectra. In one embodiment as described herein, the scans may be selected by finding the scan or time at which each group maximizes the correlation value by adding the rows of the data matrix for each group and selecting the scan with the maximum intensity value.

The foregoing processing techniques described herein, for example, in connection with flowchart 400, may not be used in instances where there are two or more molecules that elute at the same time and also have the same elution profile. In this instance, the foregoing processing steps are not able to identify the different peptides and properly pair parent (U spectra) with fragments (F spectra), and another processing technique may be used, for example, as described in U.S. patent application Ser. No. 10/388,088, filed Mar. 13, 2003, entitled "Methods and Devices for Identifying Biopolymers Using Mass Spectroscopy", hereinafter referred to as "the Thompson and Fischer disclosure". The processing steps of Thompson and Fischer may be performed on the results produced by processing steps described herein to resolve the parent-fragment pairings in instances where two or more molecules elute at the same time. The Thompson and Fischer disclosure describes a method for gathering structural information for biopolymers in a sample by running the mass spectrometer in the alternating scan mode, as described elsewhere herein, with alternating U and F spectra. Alternating scan mode provides for taking a first spectrum (U spectrum) at normal energy levels, such that fragmentation is not induced, and then a next second scan is taken at high fragmentation energy levels (F spectrum) where energy is injected by increased voltage differential between components of the ionization source, frequency stimulation, or some other technique producing a sequence of alternating spectra that can be deconvolved or decomposed to associate the appropriate fragment ions from the F spectrum with the proper parent in the U spectrum. When using an input data set that includes alternating scan mode data, the technique described herein may be a preprocessing step performed prior to the method described in the Thompson and Fischer disclosure to associate the proper parent with the fragments (pairings of U and F spectra). Charge assignment, isotope clustering, de novo sequencing, data base searching, and the like may subsequently be performed.

A U spectrum includes peaks that correspond to some and preferably all of the polypeptides in the sample when these polypeptides are unfragmented. A U spectrum may be obtained by detecting the polypeptides in the sample without exposing them to a fragmentation mechanism. It is to be understood that a U spectrum may, in certain embodiments, include peaks that represent fragments of these polypeptides, e.g., fragments that were inadvertently created as a consequence of the mechanism used to ionize and/or detect the polypeptides in the spectrometer.

An F spectrum includes peaks that correspond to a collection of fragments of some and preferably all of the polypeptides in the sample. An F spectrum may be obtained by detecting the polypeptides in the sample after these have been exposed to one or more fragmentation mechanisms. It is to be understood that an F spectrum may, in certain embodiments, include peaks that represent unfragmented polypeptides, e.g., polypeptides that survive exposure to the fragmentation mechanism. It will be appreciated that such situations are most likely to occur when the polypeptides are exposed to relatively low fragmentation energies.

The processing techniques described herein may also be performed using input data sets with multimodal chromoatograms characterized as ions or sets of ions of the same m/z value but having different chemical compositions. Graphically, a multimodal curve has multiple peaks, for example, such as if curve 3 of FIG. 9 had multiple peaks rather than the single peak as shown in the display 350. An additional step to the flowchart 10 may be used to detect multimodal curves, for example, prior to step 406 where correlation is performed. In the event the multimodal curves are determined, additional processing is performed on the input data sets. In particular, additional processing is performed prior to performing step 406 and as part of constructing the resultant spectra at step 414. This additional and modified processing is described in following paragraphs.

Multimodal peaks may be detected by using a peak finding technique which determines that a particular row of the original input data set has multiple peaks in a single curve. Although any one of a variety of different techniques may be used, one embodiment detects peaks by first filtering a row so that a baseline is removed causing peaks to be separated by zero values. An end of a peak may be determined by finding the scan at which the first derivative indicating slope of a line, is negative. If multimodal curves are determined in a particular row of the original data set, prior to performing correlation step 406, the two curves may be separated by, for example, splitting the row of original data into multiple rows, one for each additional peak. The row is split after each peak in the chromatogram. The remaining entries in each row may be zero filled. Alternatively, an embodiment may utilize other techniques, such as interpolation and curve fitting techniques, to fill in the remaining entries For example, consider a row of data in the original data matrix as described herein as follows:

otherwise determined in accordance with particular techniques, such as curve fitting and interpolation, to correct the curves and provide missing data elements. Different curve fitting techniques are well known and described, for example, in the text by C. Daniel and F. S. Wood, "Fitting Equations to Data" John Wiley and Sons, New York, 1980.

An embodiment may include a multimodal detection and correction technique that may be implemented using hardware and/or software. This row splitting allows a single chromatogram to be a member of multiple groups.

Another embodiment may include the use of image processing algorithms, such as the watershed algorithm, to perform peak finding in the time and m/z dimensions simultaneously. This approach would avoid the need to perform the aforementioned technique of peak splitting by performing the peak finding. Additionally, it would serve to partition the dataset into peaks, thereby reducing the size of the correlation matrix. This algorithm as well as other image processing techniques are described in K. R. Castleman, "Digital Image Processing" Prentice-Hall Inc., New Jersey 1996.

In connection with step 414 processing to produce a resultant spectra, the original data set is again utilized. In particular, as described elsewhere herein, the appropriate columns of intensities for the selected scans are obtained from the original data set. With multimodal data, it should be noted that an m/z range may appear in more than one group.

An embodiment may utilize any one of different types of mass spectra that may be produced, for example, by a time-of-flight (TOF) mass spectrometer. An example embodiment may use include a step following step 402 in which input data sets are converted to a more compact form prior to be used with the foregoing processing steps. For example, a TOF data set may be converted to be utilized with the foregoing techniques. The TOF input data set may be a 2-dimensional matrix with the Y-axis indicating the time of flight correlating directly to the m/z values and the elution time on the x-axis. Each column of the TOF data is a scan of the mass spectrum data. This matrix may be converted into a sparser form to minimize storage. The compaction technique used on the matrix may vary in accordance with the functionality and particular components included in each embodiment. One example embodiment utilizes a MATLAB function to compress the matrix into a sparse matrix format. Any needed subsequent conversions may be performed by MATLAB. An embodiment may optionally use other formats depending on memory constraints and other characteristics of an embodiment.

An embodiment may utilize filtering techniques to reduce noise and eliminate data associated with known contaminants. For example, particular correlation values of a known contaminant within a certain m/z range may be eliminated at

| entry# | 1 | 2 | 3 | 4 | 5 | 6 | 7 | 8 | 9 | 10 | n |
|---|---|---|---|---|---|---|---|---|---|---|---|
| | 0 | 3.0 | 2.4 | 10.0 | 3.0 | 1.0 | 4.0 | 20.0 | 2.2 | 3.4 | ... | and that the peak finding technique determines that there a multiple peaks corresponding to elements 4 and 8 above with values, respectively, of 10.0 and 20.0. One example embodiment may, in this instance, split the foregoing row of data into two rows with a first row including elements 1 through 6, and a second row including elements 6—n. The remaining elements in the first and second rows may be zero filled or step 408. Consider, for example, that a known detergent contaminant may be present. The contaminant presence may be determined by manually examining a contour plot and visually locating a constant horizontal band present at all elution times. Input data sets may be examined to automatically test for known contaminants and accordingly remove the bands of data. It should be noted that an example embodiment may provides for "noise" to be filtered that is highly correlated, such as a known contaminant, and/or weakly correlated, such as interference.

It should be noted that the techniques described herein may be used for performing a quantitative analysis rather than for identification processing, for example, such as identifying matching F and U spectra. This may affect the previously described processing steps. When performing a quantitative analysis using the foregoing techniques, points of interest selected, as at step 412, may include those sampled frequently across each group, rather than determining a single maximum as described herein. As described elsewhere herein, step 414 processing produces a single spectra for each ion with contaminants and other covarying spectra removed. For quantitative analysis using the foregoing techniques, a spectrum is produced for each cluster or group. For quantitation, the peak areas are integrated for the group chromatograms or rows. This provides a group peak area that may be used for relative quantitation with other groups in the data set. For quantitation, each cluster or group using the foregoing techniques represents a range of m/z values and elution time that contains related signal.

The foregoing provides techniques utilizing the fact that certain groupings tend to covary. Parent and related ion fragments tend to covary and exhibit similar coelution profiles. Input data including only U spectra, when processed by the techniques described herein, may be used to group charge states and isotopes of single peptides since these charge states and isotopes covary by coeluting at the same time. Input data including only F spectra may be used to group charge state, isotopes and fragments that coelute at the same time. The foregoing may also be used as a preprocessing step in connection with the Thompson and Fischer disclosure and other processing techniques to identify U and related F spectra when two parent or U spectra within a group have the same elution profile and coelute at the same time. Such other techniques may include, for example, identification algorithms, such as SEQUEST, MASCOT, MSFIT, and the like. These techniques are known in the art. For example, SEQUEST is described in: Eng, J. K.; McCormack, A. L.; Yates J. R. III. *J. Am. Soc. Mass Spectrom.* 1994, 5, 976-989; MASCOT is described in: Perkins, D. N.; Pappin, D. J. C.; Creasy, D. M.; Cottrell, J. S. *Electrophoresis* 1999, 20, 3551-3567; and MSFIT is described in: Clauser K. R., Baker P. R. and Burlingame A. L., Role of accurate mass measurement (+/−10 ppm) in protein identification strategies employing MS or MS/MS and database searching. *Analytical Chemistry*, Vol. 71, 14, 2871-(1999).

Use of the Thompson and Fischer disclosure and/or other technique may be used to distinguish between two unrelated components (not isotopes, charge states or fragments) that coelute and exactly covary since the techniques described herein will not be able to distinguish between two such unrelated compounds. Different techniques may be used to determine the existence of such a condition indicating a need to invoke alternative techniques to assign these parents to their corresponding fragments. An embodiment may test extracted U spectra for the presence of multiple parents which the foregoing techniques cannot distinguish between as follows. Deisotoping and charge deconvolution may be performed on the spectrum resulting in a neutral mass spectrum (not m/z). The multiple isotopic distributions for each charge state of a single peptide or component are collapsed into a single mass peak. Senko, M. W., Beu, S. C., McLafferty, F. W. *J. Mass Spectrom*, Vol 6, 52-(1995). Thus, if two peptides or components are present in an extracted U spectrum, this deconvolution procedure results in two mass peaks indicating the need to invoke additional processing, such as the Thompson and Fischer method, to match each parent with associated fragment ions.

The foregoing provides techniques for analyzing the chromatographic information of a data set, such as an LC/MS data set to separate related ions into spectra representing individual compounds and identifying the specific spectra that provide maximum signal levels for subsequent analysis. Additionally, the foregoing removes noise from the data set since noise does not tend to covary with the real data signals. Constant signals resulting from contaminants may also tend not to covary with the real data signals and may also drop out. Since noise is removed using the foregoing techniques in addition to any specific filtering techniques applied, for example, at step 404 processing, performance of subsequent processing, such as de novo sequencing, may be significantly improved. The foregoing also may result in a reduction in the size and complexity of an input data set used in subsequent processing. The foregoing techniques may be used in protein identification, but may also be applied to other classes of molecules sharing similar characteristics such as, for example, polynucleotides, polysaccharides and other small molecules.

While the invention has been disclosed in connection with preferred embodiments shown and described in detail, their modifications and improvements thereon will become readily apparent to those skilled in the art. Accordingly, the scope of the present invention should be limited only by the following claims.

What is claimed is:

1. A method for identifying related ions in an input data set of spectra produced by analyzing a sample comprising:
   correlating each row of data in an input data set with every other row of data in said input data set producing a correlation matrix composed of elements, each row representing ion intensities over time for a particular range of values, said values representing mass-to-charge (m/z) ratios of said ions, each element of said correlation matrix including a correlation value and having associated row and column identifiers identifying which rows in said input data set are associated with said correlation value, wherein said correlation value indicates a degree to which rows identified by said row and column identifiers are related to one another;
   clustering said correlation matrix identifying at least one group of correlated ranges of said values, wherein at least one row of said correlation matrix is identified as being in said at least one group, each group representing covarying ion chromatograms over a plurality of time periods;
   selecting at least one time period of interest for each group; and
   producing and outputting to a user a resultant spectrum identifying related ions for each group by sampling said ion chromatograms included in each of said groups at each of said at least one time period of interest.

2. The method of claim 1, further comprising:
   filtering said input data set prior to performing said correlation.

3. The method of claim 1, wherein said input data set includes only one of: unfragmented spectrum, fragmented spectrum, and alternating unfragmented and fragmented spectrum.

4. The method of claim 3, wherein said input data set includes only alternating unfragmented and fragmented spectra, and the method further comprising:
   forming a combined spectrum including an unfragmented spectrum and related fragmented spectrum;
   performing said correlating, said clustering, said selecting and said producing using said combined spectrum;
   determining m/z values in said combined spectrum;

sampling said unfragmented spectra at said m/z values in said combined spectrum at a scan maximum identified for said combined spectrum; and determining that a sampled m/z value in said combined spectra is associated with a parent if there is an intensity at said sampled m/z value, and determining that said sampled m/z value in said combined spectra is associated with a fragment in an absence of a signal at said sampled m/z value.

5. The method of claim 3, wherein said input data set includes only alternating unfragmented and fragmented spectra, and the method further comprising:

performing said correlating, said clustering, said selecting and said producing using each of said unfragmented spectrum and said fragmented spectrum separately; and matching each parent of said unfragmented spectrum to related fragments in said fragmented spectrum by determining which of said related fragments covary with said parent.

6. The method of claim 1, wherein said clustering further comprises:

determining a first row of said correlation matrix including an element having a maximum correlation value of all correlation values in the correlation matrix being considered as candidates to be grouped;

determining a time scan associated with said first row;

for each element of said first row corresponding to a unique pairing of a row "i" and column "j", determining if a correlation value is greater than a predetermined value and determining if a scan number at which row "j" maximizes is within a threshold number of scans of said time scan associated with said first row; and if said each element is greater than said predetermined value and if a scan number at which row "j" maximizes is within a threshold number of scans of said time scan associated with said first row, adding a row of said input data set to a current group wherein the row added has a row number equal to that of a column index "j" associated with said each element, and excluding the row added from further consideration as one of said candidates for grouping.

7. The method of claim 6, further comprising:

performing said determining a first row if a correlation value is greater than a predetermined value and if a scan number at which row "j" maximizes is within a threshold number of scans of said time scan associated with said first row for each element of the first row having an associated column index greater than an index associated with said first row.

8. The method of claim 7, further comprising:

stopping formation of groups by said clustering when said maximum correlation value is less than a predetermined value.

9. The method of claim 8, further comprising:

forming a new group with a selection of a subsequent row including an element having a maximum correlation value of all correlation values in the correlation matrix being considered as candidates to be grouped.

10. The method of claim 3, wherein said input data set includes only alternating unfragmented and fragmented spectra, said input data set includes at least two components eluting at a same time and having a same elution profile, and the method further comprising:

combining adjacent fragmented and unfragmented spectra resulting in a new combined data set including half the number of spectra in comparison to a total of spectra of said fragmented and unfragmented spectra;

producing a first resulting spectrum and a second resulting spectrum, said first resulting spectrum corresponding to said unfragmented spectrum at a selected point in time and said second resulting spectrum corresponding to said fragmented spectrum at said selected point in time; and performing processing to identify which of said at least two components is a parent associated with at least one fragment included in said fragmented spectrum.

11. The method of claim 3, wherein said input data set includes only unfragmented spectrum, and said at least one group formed by said clustering identifies charge states and isotopes of a single component that coelute at a same time.

12. The method of claim 3, wherein said input data set includes only fragmented spectrum, and said at least one group formed by said clustering identifies charge states, isotopes, and fragments of a single component that coelute at a same time.

13. The method of claim 1, wherein said selecting time periods of interest includes:

summing intensities of extracted chromatograms for each group at each scan point; and determining a maximum intensity for each group at a particular scan point; and wherein said producing the resultant spectrum includes:

sampling the extracted ion chromatograms of each group at said particular scan point.

14. The method of claim 1, wherein said input data set is produced using a mass spectrometer analyzing the sample.

15. The method of claim 1, wherein said input data set includes at least one multimodal peak of an extracted ion chromatogram, a number of peaks in said multimodal peak being represented as "n", and the method further comprising:

determining at least one split point in said multimodal peak to divide said multimodal peak into portions;

apportioning a first row of said input data set corresponding to said multimodal peak into row portions in accordance with said at least one split point;

creating an additional "n−1" rows of data included in said input data set, each of said additional rows including a different one of said row portions;

removing from said first row all row portions included in said additional rows; and filling remaining elements of each of said additional rows and said first row.

16. The method of claim 1, further comprising:

filtering said input data set producing a filtered data set, and wherein said form of said input data set is said filtered data set.

17. The method of claim 10, wherein at least two ions are two parent ions co-eluting at a same time having a same elution profile and covary, and the method further comprising:

performing other processing steps to associate each of said two parent ions with corresponding fragment ions.

18. The method of claim 10, wherein said at least two components are parent peptides that coelute at a same time and exhibit similar elution profiles, and the method further comprising:

determining that additional processing is needed to match each of said at least two parent peptides with associated child fragments; and performing said additional processing.

19. The method of claim 10, wherein said at least two components are peptides.

20. A method for quantifying at least one ion in an input data set of spectra produced by analyzing a sample comprising:
- correlating each row of data in an input data set with every other row of data in said input data set producing a correlation matrix composed of elements, each row representing ion intensities over time for a particular range of values, said values representing mass to charge (m/z) ratios of said ions, each element of said correlation matrix including a correlation value and having associated row and column identifiers identifying which rows in said input data set are associated with said correlation value wherein said correlation value indicates a degree to which rows identified by said row and column identifiers are related to one another;
- clustering said correlation matrix and identifying at least one group of correlated ranges of said values, wherein at least one row of said correlation matrix is identified as being in said at least one group, each group representing ions of chemically related components exhibiting correlated chromatographic behavior each group providing values over a plurality of time periods;
- selecting at least one time period of interest for each group; and
- producing and outputting to a user a resultant spectrum quantifying at least one ion for each group by sampling ion chromatograms included in each of said groups at each of said at least one time period of interest.

21. A program embodied in a computer-readable medium for identifying related ions in an input data set of spectra produced by analyzing a sample comprising:
- machine executable code that correlates each row of data in an input data set with every other row of data in said input data set producing a correlation matrix composed of elements, each row representing ion intensities over time for a particular range of values, said values representing mass to charge (m/z) ratios of said ions, each element of said correlation matrix including a correlation value and having associated row and column identifiers identifying which rows in said input data set are associated with said correlation value wherein said correlation value indicates a degree to which rows identified by said row and column identifiers are related to one another;
- machine executable code that clusters said correlation matrix identifying at least one group of correlated ranges of said values, wherein at least one row of said correlation matrix is identified as being in said at least one group, each group representing covarying ion chromatograms over a plurality of time periods;
- machine executable code that selects at least one time period of interest for each group; and
- machine executable code that produces and outputs to a user a resultant spectrum identifying related ions for each group by sampling said ion chromatograms included in each of said groups at each of said at least one time period of interest.

22. The program embodied in the computer-readable medium of claim 21, further comprising:
- machine executable code that filters said input data set prior to performing said correlation.

23. The program embodied in the computer-readable medium of claim 21, wherein said input data set includes only one of: unfragmented spectrum, fragmented spectrum, and alternating unfragmented and fragmented spectrum.

24. The program embodied in the computer-readable medium of claim 23, wherein said input data set includes only alternating unfragmented and fragmented spectra, and the program embodied in the computer-readable medium further comprising:
- machine executable code that forms a combined spectrum including an unfragmented spectrum and related fragmented spectrum and wherein said machine executable code that correlates, clusters, selects and produces uses said combined spectrum;
- machine executable code that determines m/z values in said combined spectrum;
- machine executable code that samples said unfragmented spectra at said m/z values in said combined spectrum at a scan maximum identified for said combined spectrum; and
- machine executable code that determines that a sampled m/z value in said combined spectra is associated with a parent if there is an intensity at said sampled m/z value, and determines that said sampled m/z value in said combined spectra is associated with a fragment in an absence of a signal at said sampled m/z value.

25. The computer program product of claim 23, wherein said input data set includes only alternating unfragmented and fragmented spectra, said machine executable code that correlates, clusters, selects and produces uses each of said unfragmented spectrum and said fragmented spectrum separately; and the computer program product further comprising: machine executable code that matches each parent of said unfragmented spectrum to related fragments in said fragmented spectrum by determining which of said related fragments covary with said parent.

26. The program embodied in the computer-readable medium of claim 21, wherein said clustering further comprises:
- machine executable code that determines a first row of said correlation matrix including an element having a maximum correlation value of all correlation values in the correlation matrix being considered as candidates to be grouped;
- machine executable code that determines a time scan associated with said first row;
- machine executable code that, for each element of said first row corresponding to a unique pairing of a row "i" and column "j", determines if a correlation value is greater than a predetermined value and determining if a scan number at which row "j" maximizes is within a threshold number of scans of said time scan associated with said first row; and
- machine executable code that, if said each element is greater than said predetermined value and if a scan number at which row "j" maximizes is within a threshold number of scans of said time scan associated with said first row, adds a row of said input data set to a current group wherein the row added has a row number equal to that of a column index "j" associated with said each element, and excluding the row added from further consideration as one of said candidates for grouping.

27. The program embodied in the computer-readable medium of claim 26, further comprising:
- machine executable code that determines said first row if a correlation value is greater than a predetermined value and if a scan number at which row "j" maximizes is within a threshold number of scans of said time scan associated with said first row for each element of the first row having an associated column index greater than an index associated with said first row.

28. The program embodied in the computer-readable medium of claim 27, further comprising:
  machine executable code that stops formation of groups by said clustering when said maximum correlation value is less than a predetermined value.

29. The program embodied in the computer-readable medium of claim 28, further comprising:
  machine executable code that forms a new group with a selection of a subsequent row including an element having a maximum correlation value of all correlation values in the correlation matrix being considered as candidates to be grouped.

30. The program embodied in the computer-readable medium of claim 23, wherein said input data set includes only alternating unfragmented and fragmented spectra, said input data set includes at least two components eluting at a same time and having a same elution profile, and the program embodied in the computer-readable medium further comprising:
  machine executable code that combines adjacent fragmented and unfragmented spectra resulting in a new combined data set including half the number of spectra in comparison to a total of spectra of said fragmented and unfragmented spectra;
  machine executable code that produces a first resulting spectrum and a second resulting spectrum, said first resulting spectrum corresponding to said unfragmented spectrum at a selected point in time and said second resulting spectrum corresponding to said fragmented spectrum at said selected point in time; and
  machine executable code that performs processing to identify which of said at least two components is a parent associated with at least one fragment included in said fragmented spectrum.

31. The computer program product of claim 23, wherein said input data set includes only unfragmented spectrum, and said at least one group formed by said clustering identifies charge states and isotopes of a single component that coelute at a same time.

32. The program embodied in the computer-readable medium of claim 23, wherein said input data set includes only fragmented spectrum, and said at least one group formed by said clustering identifies charge states, isotopes, and fragments of a single component that coelute at a same time.

33. The program embodied in the computer-readable medium of claim 21, wherein said selecting time periods of interest includes:
  machine executable code that sums intensities of extracted ion chromatograms for each group at each scan point; and
  machine executable code that determines a maximum intensity for each group at a particular scan point; and wherein said producing the resultant spectrum includes:
  machine executable code that samples the extracted ion chromatograms of each group at said particular scan point.

34. The program embodied in the computer-readable medium of claim 21, wherein said input data set is produced using a mass spectrometer analyzing the sample.

35. The program embodied in the computer-readable medium of claim 21, wherein said input data set includes at least one multimodal peak, wherein said input data set includes at least one multimodal peak of an extracted ion chromatogram, a number of peaks in said multimodal peak being represented as "n", and the program embodied in the computer-readable medium further comprising:
  machine executable code that determines at least one split point in said multimodal peak to divide said multimodal peak into portions;
  machine executable code that apportions a first row of said input data set corresponding to said multimodal peak into row portions in accordance with said at least one split point;
  machine executable code that creates an additional "n−1" rows of data included in said input data set, each of said additional rows including a different one of said row portions;
  machine executable code that removes from said first row all row portions included in said additional rows; and
  machine executable code that fills remaining elements of each of said additional rows and said first row.

36. The program embodied in the computer-readable medium of claim 21, further comprising:
  machine executable code that filters said input data set producing a filtered data set, and wherein said form of said input data set is said filtered data set.

37. The program embodied in the computer-readable medium of claim 30, wherein at least two ions are two parent ions co-eluting at a same time having a same elution profile and covary, and the program embodied in the computer-readable medium further comprising:
  machine executable code that performs other processing steps to associate each of said two parent ions with corresponding fragment ions.

38. The program embodied in the computer-readable medium of claim 30, wherein said at least two components are parent peptides that coelute at a same time and exhibit similar elution profiles, and the program embodied in the computer-readable medium further comprising:
  machine executable code that determines that additional processing is needed to match each of said at least two parent peptides with associated child fragments; and
  machine executable code that performs said additional processing.

39. The program embodied in the computer-readable medium of claim 29, wherein said at least two components are peptides.

40. A program embodied in the computer-readable medium for quantifying at least one ion in an input data set produced by analyzing a sample comprising:
  machine executable code that correlates each row of data in an input data set with every other row of data in said input data set producing a correlation matrix, each row representing ion intensities over time for a particular range of values, said values representing mass to charge (m/z) ratios of said ions, each element of said correlation matrix including a correlation value and having associated row and column identifiers identifying which rows in said input data set are associated with said correlation value;
  machine executable code that clusters said correlation matrix identifying at least one group and at least one row of said correlation matrix as being in said at least one group, each group representing ions of chemically related components exhibiting correlated chromatographic behavior;
  machine executable code that selects at least one time period of interest for each group; and
  machine executable code that produces and outputs to a user a resultant spectrum quantifying at least one ion for each group by sampling ion chromatograms included in each of said groups at each of said at least one time period of interest of using a form of said input data set.

* * * * *